United States Patent
Huang et al.

(10) Patent No.: US 9,540,619 B2
(45) Date of Patent: Jan. 10, 2017

(54) MELK REGULATION FOR THE TREATMENT OF BREAST CANCER

(71) Applicants: NOVARTIS AG, Basel (CH); DANA-FARBER CANCER INSTITUTE, INC., Boston, MA (US)

(72) Inventors: Xizhong Huang, Cambridge, MA (US); Jean J. Zhao, Brookline, MA (US); Junxia Min, Cambridge, MA (US); Yubao Wang, Newton, MA (US)

(73) Assignees: Novartis AG, Basel (CH); Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/759,889

(22) PCT Filed: Jan. 8, 2014

(86) PCT No.: PCT/US2014/010724
§ 371 (c)(1),
(2) Date: Jul. 8, 2015

(87) PCT Pub. No.: WO2014/110163
PCT Pub. Date: Jul. 17, 2014

(65) Prior Publication Data
US 2015/0353935 A1 Dec. 10, 2015

Related U.S. Application Data

(60) Provisional application No. 61/751,703, filed on Jan. 11, 2013.

(51) Int. Cl.
| | | |
|---|---|---|
| C12N 15/113 | (2010.01) | |
| C12N 9/12 | (2006.01) | |
| A61K 38/12 | (2006.01) | |
| A61K 31/7088 | (2006.01) | |
| C12Q 1/68 | (2006.01) | |

(52) U.S. Cl.
CPC ............ *C12N 9/12* (2013.01); *A61K 31/7088* (2013.01); *A61K 38/12* (2013.01); *C12N 15/1135* (2013.01); *C12N 15/1137* (2013.01); *C12Q 1/6886* (2013.01); *C12Y 207/11001* (2013.01); *C12N 2310/14* (2013.01); *C12N 2310/531* (2013.01); *C12Q 2600/158* (2013.01)

(58) Field of Classification Search
CPC ................. C12N 15/1135; A61K 31/7088
See application file for complete search history.

(56) References Cited

FOREIGN PATENT DOCUMENTS

WO WO 2004/070062 A2 8/2004

OTHER PUBLICATIONS

Altschul et al.; "Gapped BLAST and PSI-BLAST: a new generation of protein database search programs"; Nucleic Acids Research, vol. 25, No. 17; Sep. 17, 1997; pp. 3389-3402.
Badouel et al.; "Maternal embryonic leucine zipper kinase is stabilized in mitosis by phosphorylation and is partially degraded upon mitotic exit"; Experimental Cell Research, vol. 316; Aug. 2010; pp. 2166-2173.
Bernstein et al.; "Role for a bidentate ribonuclease in the initiation step of RNA interference"; Nature, vol. 409; Jan. 18, 2001; pp. 363-366.
Beullens et al.; "Substrate Specificity and Activity Regulation of Protein Kinase MELK"; The Journal of Biological Chemistry, vol. 280, No. 48; Dec. 2, 2005; pp. 40003-40011.
Bischoff et al.; "A homologue of *Drosophila aurora* kinase is oncogenic and amplified in human colorectal cancers"; The EMBO Journal, vol. 17, No. 11; Jun. 1, 1998; pp. 3052-3065.
Boehm et al.; "Integrative Genomic Approaches Identify IKBKE as a Breast Cancer Oncogene"; Cell, vol. 129; Jun. 15, 2007; pp. 1065-1079.
Cordes et al.; "The *C. elegans* MELK ortholog PIG-1 regulates cell size asymmetry and daughter cell fate in asymmetric neuroblast divisions"; Development, vol. 133, No. 14; Jul. 15, 2006; pp. 2747-2756.
Dar et al.; "Aurora Kinase Inhibitors—Rising Stars in Cancer Therapeutics?"; Mol Cancer Ther, vol. 9, No. 2; Feb. 2010; pp. 268-278.
Davezac et al.; "Human pEg3 kinase associates with and phosphorylates CDC25B phosphatase: A potential role for pEg3 in cell cycle regulation"; Oncogene, vol. 21; Nov. 2002; pp. 7630-7641.
Desmedt et al.; "Strong Time Dependence of the 76-Gene Prognostic Signature for Node-Negative Breast Cancer Patients in the TRANSBIG Multicenter Independent Validation Series"; Clin Cancer Res, vol. 13, No. 11; Jun. 1, 2007; pp. 3207-3214.

(Continued)

*Primary Examiner* — Jon E Angell
(74) *Attorney, Agent, or Firm* — Brinks Gilson & Lione

(57) ABSTRACT

Methods for inhibiting growth or proliferation of breast cancer cells are provided. The methods include administering to a subject in need thereof in an amount that is effective to inhibit growth or proliferation of the breast cancer cells a MELK inhibitor, wherein the breast cancer cells are estrogen receptor (ER) negative. In some aspects, the methods include administering to a subject in need thereof in an amount that is effective to inhibit growth or proliferation of the breast cancer cells a MELK inhibitor, a FoxM1 inhibitor or a MELK inhibitor and a FoxM1 inhibitor, wherein the breast cancer cells are estrogen receptor (ER) negative. Methods of treatment for breast cancer and methods of identifying patients having cancer that are likely to benefit from treatment with a MELK inhibitor, a FoxM1 inhibitor or a MELK inhibitor and a FoxM1 inhibitor are also provided.

7 Claims, 23 Drawing Sheets

(56) References Cited

OTHER PUBLICATIONS

Di Fiore et al.; "erbB-2 is a potent oncogene when overexpressed in NIH/3T3 cells"; Science, vol. 237, Jul. 10, 1987 pp. 178-182.
Elbashir et al., "Duplexes of 21-nucleotide RNAs mediate RNA interference in cultured mammalian cells"; Nature, vol. 411; May 24, 2001; pp. 494-498.
Elbashir et al.; Functional anatomy of siRNAs for mediating efficient RNAi in *Drosophila melanogaster* embryo lysate; The EMBO Journal, vol. 20, No. 23; Dec. 1, 2001; pp. 6877-6888.
Esserman et al.; "Chemotherapy response and recurrence free survival in neoadjuvant breast cancer depends on biomarker profiles: results from the I-Spy 1 Trial (CALGB 150007/150012; ACRIN 6657)"; Breast Cancer Res Treat, vol. 132, Issue 3; Apr. 2012; pp. 1049-1062.
Fire et al., "Potent and specific genetic interference by double-stranded RNA in *Caenorhabditis elegans*"; Nature, vol. 391; Feb. 19, 1998; pp. 806-811.
Foulkes et al.; "Triple-negative breast cancer"; New England Journal of Medicine, vol. 363, Nov. 11, 2010; pp. 1938-1948.
Golsteyn et al.; "Cell cycle analysis and chromosomal localization of human Plk1, a putative homologue of the mitotic kinases *Drosophila polo* and *Saccharomyces cerevisiae* Cdc5"; Journal of Cell Science, vol. 107; Jun. 1, 1994; pp. 1509-1517.
Gray, et al.; "Maternal Embryonic Leucine Zipper Kinase/Murine Protein Serine-Threonine Kinase 38 Is a Promising Therapeutic Target for Multiple Cancers"; Cancer Res, vol. 65, No. 1; Nov. 1, 2005; pp. 9751-9761.
Hahn et al.; "Creation of human tumour cells with defined genetic elements"; Nature, vol. 400, Jul. 29, 1999; pp. 464-468.
Hatzis et al.; "A genomic predictor of response and survival following taxane-anthracycline chemotherapy for invasive breast cancer"; JAMA, vol. 305, No. 18; May 11, 2011; pp. 1873-1881.
Hegde et al.; "The transcription factor FOXM1 is a cellular target of the natural product thiostrepton"; Nature Chemistry, vol. 3, Aug. 21, 2011; pp. 725-731.
Henikoff et al.; "Amino acid substitution matrices from protein blocks"; Proc. Natl. Acad. Sci. USA, vol. 89; Nov. 1992; pp. 10915-10919.
Hinds et al.; "Function of a human cyclin gene as an oncogene" Proc. Natl. Acad. Sci. USA, vol. 91; Jan. 1994; pp. 709-713.
Hudziak et al.; "Increased expression of the putative growth factor receptor p185HER2 causes transformation and tumorigenesis of NIH 3T3 cells"; Proc. Natl. Acad. Sci. USA, vol. 84; Oct. 1987; pp. 7159-7163.
Kanda et al.; "Histone-GFP fusion protein enables sensitive analysis of chromosome dynamics in living mammalian cells"; Current Biology; vol. 8; Mar. 10, 1998; pp. 377-385.
Kao et al.; "Correlation of microarray-based breast cancer molecular subtypes and clinical outcomes: implications for treatment optimization"; BMC Cancer, vol. 11; Apr. 18, 2011; 15 pages.
Karlin et al.; "Applications and statistics for multiple high-scoring segments in molecular sequences"; Proc. Nat'l. Acad. Sci. USA, vol. 90; Jun. 1993; pp. 5873-5787.
Keen et al.; "Mitotic drivers—inhibitors of the Aurora B Kinase"; Cancer Metastasis Rev, vol. 28; Feb. 3, 2009; pp. 185-195.
Kim et al.; "CK1epsilon is required for breast cancers dependent on betacatenin activity"; PLoS One, vol. 5, Issue 2; Feb. 2010; ten pages.
Kittler et al.; "An endoribonuclease-prepared siRNA screen in human cells identifies genes essential for cell division"; Nature, vol. 432; pp. 1036-1040.
Koboldt et al.; "Comprehensive molecular portraits of human breast tumours"; Nature, vol. 490; Oct. 4, 2012; pp. 61-70.
Krause et al.; "Tyrosine kinases as targets for cancer therapy"; N Engl J Med, vol. 353, Jul. 14, 2005; pp. 172-187.
Laoukili et al.; "FoxM1 is required for execution of the mitotic programme and chromosome stability"; Nature Cell Biology, vol. 7, Feb. 2005; pp. 126-136.

Le Page et al.; "A functional analysis of MELK in cell division reveals a transition in the mode of cytokinesis during Xenopus development"; Journal of Cell Science, vol. 124; Mar. 15, 2011; pp. 958-968.
Lee et al.; "Chromatin immunoprecipitation and microarray-based analysis of protein location"; Nature Protocols, vol. 1, Jul. 13, 2006; pp. 729-748.
Lefebvre et al.; "A human B-cell interactome identifies MYB and FOXM1 as master regulators of proliferation in germinal centers"; Molecular Systems Biology, vol. 6, Article No. 377; Jan. 1, 2010; ten pages.
Lens et al.; "Shared and separate functions of polo-like kinases and aurora kinases in cancer"; Nature Reviews—Cancer, vol. 10, Dec. 2010; pp. 825-841.
Lin et al.; "Involvement of maternal embryonic leucine zipper kinase (MELK) in mammary carcinogenesis through interaction with Bcl-G, a pro-apoptotic member of the Bcl-2 family"; Breast Cancer Research, vol. 9, Feb. 6, 2007; 13 pages.
Liu et al.; "Normal cells, but not cancer cells, survive severe Plk1 depletion"; Molecular and Cellular Biology, vol. 26; Mar. 2006; pp. 2093-2108.
Lizcano et al.; "LKB1 is a master kinase that activates 13 kinases of the AMPK subfamily, including MARK/PAR-1"; The EMBO Journal, vol. 23, Feb. 19, 2004; pp. 833-843.
Loi et al.; "Definition of clinically distinct molecular subtypes in estrogen receptor-positive breast carcinomas through genomic grade"; Journal of Clinical Oncology, vol. 25; Apr. 1, 2007; pp. 1239-1246.
Ma et al.; "Gene expression profiling of the tumor microenvironment during breast cancer progression"; Breast Cancer Research, vol. 11; Feb. 2, 2009; 18 pages.
Nakano et al.; "Maternal embryonic leucine zipper kinase (MELK) regulates multipotent neural progenitor proliferation"; The Journal of Cell Biology, vol. 170, Aug. 1, 2005; pp. 413-427.
Nakano et al.; "Maternal embryonic leucine zipper kinase is a key regulator of the proliferation of malignant brain tumors, including brain tumor stem cells"; Journal of Neuroscientific Research, vol. 86, Jan. 2008; pp. 48-60.
Nassirpour et al.; "Nek6 mediates human cancer cell transformation and is a potential cancer therapeutic target"; Molecular Cancer Research, vol. 8; Apr. 20, 2010; pp. 717-728.
Neve et al.; "A collection of breast cancer cell lines for the study of functionally distinct cancer subtypes"; Cancer Cell, vol. 10, Dec. 2006; pp. 515-527.
Ni et al.; "Functional characterization of an isoform-selective inhibitor of PI3K-p110beta as a potential anticancer agent"; Cancer Discovery, vol. 2, Apr. 12, 2012; pp. 425-433.
Parker et al.; "Supervised risk predictor of breast cancer based on intrinsic subtypes" Journal of Clinical Oncology, vol. 27, Mar. 10, 2009; pp. 1160-1167.
Pawitan et al.; "Gene expression profiling spares early breast cancer patients from adjuvant therapy: derived and validated in two population-based cohorts"; Breast Cancer Research, vol. 7, Oct. 3, 2005; pp. 953-964.
Perou et al.; "Molecular portraits of human breast tumours"; Nature, vol. 406, Aug. 2000; pp. 747-752.
Perou; "Molecular Stratification of Triple-Negative Breast Cancers"; The Oncologist, vol. 16, Supplement; Jan. 2011; pp. 61-70.
Pickard et al.; "Dysregulated expression of Fau and MELK is associated with poor prognosis in breast cancer"; Breast Cancer Research, vol. 11; Aug. 11, 2009; 8 pages.
Rakha et al.; "Basal-like breast cancer: a critical review"; Journal of Clinical Oncology, vol. 26; May 20, 2008; pp. 2568-2581.
Rhodes et al.; "ONCOMINE: a cancer microarray database and integrated datamining platform"; Neoplasia, vol. 6, No. 1; Jan./Feb. 2004; pp. 1-6.
Richardson et al.; "X chromosomal abnormalities in basal-like human breast cancer"; Cancer Cell, vol. 9; Feb. 2006; pp. 121-132.
Schmidt et al.; "The humoral immune system has a key prognostic impact in node-negative breast cancer"; Cancer Research, vol. 68; Jul. 1, 2008; pp. 5405-5413.

(56) References Cited

OTHER PUBLICATIONS

Seong et al.; "Murine protein serine-threonine kinase 38 activates p53 function through Ser15 phosphorylation"; Journal of Biological Chemistry, vol. 287; Jun. 15, 2012; pp. 20797-20810.

Seong et al.; "PDK1 protein phosphorylation at Thr354 by murine protein serine-threonine kinase 38 contributes to negative regulation of PDK1 protein activity"; Journal of Biological Chemistry, vol. 287; Jun. 15, 2012; pp. 20811-20822.

Sorlie et al.; "Gene expression patterns of breast carcinomas distinguish tumor subclasses with clinical implications"; Proc Natl Acad Sci USA, vol. 98; Sep. 11, 2001; pp. 10869-10874.

Sotiriou et al.; "Breast cancer classification and prognosis based on gene expression profiles from a population-based study"; Proc Natl Acad Sci USA, vol. 100; Sep. 2, 2003; pp. 10393-10398.

Stephens et al.; "The landscape of cancer genes and mutational processes in breast cancer"; Nature, vol. 486, Jun. 21, 2012; pp. 400-404.

Takahashi et al.; "Activation of a novel human transforming gene, ret, by DNA rearrangement"; Cell 42, Sep. 1985; pp. 581-588.

Taylor et al; "Polo and Aurora kinases: lessons derived from chemical biology"; Current Opinion in Cell Biology, vol. 20; Mar. 2008; pp. 77-84.

van 't Veer et al.; "Gene expression profiling predicts clinical outcome of breast cancer"; Nature, vol. 415; Dec. 4, 2002; pp. 530-536.

van de Vijver et al.; "A gene-expression signature as a predictor of survival in breast cancer"; The New England Journal of Medicine, vol. 347, Dec. 19, 2002; pp. 1999-2009.

Vazquez-Martin et al.; "AMPK: Evidence for an energy-sensing cytokinetic tumor suppressor"; Cell Cycle, vol. 8; Nov. 15, 2009; pp. 3679-3683.

Vulsteke et al.; "Inhibition of spliceosome assembly by the cell cycle-regulated protein kinase MELK and involvement of splicing factor NIPP1"; Journal of Biological Chemistry, vol. 279; Mar. 5, 2004; pp. 8642-8647.

Wang et al.; "Forkhead box M1 regulates the transcriptional network of genes essential for mitotic progression and genes encoding the SCF (Skp2-Cks1) ubiquitin ligase"; Molecular and Cellular Biology, vol. 25; Dec. 2005; pp. 10875-10894.

Wang et al; "Gene-expression profiles to predict distant metastasis of lymph-node-negative primary breast cancer"; Lancet, vol. 365; Feb. 19, 2005; pp. 671-679.

Wee et al.; "PTEN-deficient cancers depend on PIK3CB"; Proc Natl Acad Sci USA, vol. 105; Sep. 2, 2008; pp. 13057-13062.

Wiederschain et al.; "Single-vector inducible lentiviral RNAi system for oncology target validation"; Cell Cycle, vol. 8, Feb. 2009; pp. 498-504.

Wierstra et al.; "FOXM1, a typical proliferation-associated transcription factor" Biol Chem, vol. 388, Dec. 2007; pp. 1257-1274.

Yin et al.; "The serine/threonine kinase Nek6 is required for cell cycle progression through mitosis"; Journal of Biological Chemistry, vol. 278, Dec. 26, 2003; pp. 52454-52460.

Zhang et al.; "Targeting cancer with small molecule kinase inhibitors"; Nature Reviews—Cancer, vol. 9, Jan. 2009; pp. 28-39.

Zhao et al.; "Human mammary epithelial cell transformation through the activation of phosphatidylinositol 3-kinase"; Cancer Cell, vol. 3, May 2003; pp. 483-495.

Zhao et al.; "Functional genetics and experimental models of human cancer"; Trends in Molecular Medicine, vol. 10, Jul. 2004; pp. 344-350.

Zhou et al.; "Tumour amplified kinase STK15/BTAK induces centrosome amplification, aneuploidy and transformation"; Nature Genetics, vol. 20, Oct. 1998; pp. 189-193.

AJV15267 standard; "Human KIAA0175 target sequence SEQ ID No. 24776"; XP055115773; Dec. 28, 2007.

Bianchini, G. et al.; "Prognostic and Therapeutic Implications of Distinct Kinase Expression Patterns in Different Subtypes of Breast Cancer"; Cancer Research, vol. 70, No. 21; pp. 8852-8862; Nov. 1, 2010.

Chung, S. et al.; "Development of an orally-administrative MELK-targeting inhibitor that suppresses the growth of various types of human cancer"; Oncotarget, vol. 3, No. 12; pp. 1629-1640; Dec. 1, 2012.

Wheatley, K. et al.; "Abstract 1664: Maternal embryonic leucine aiper kinase (MELK) is a critical regulator of proliferation and is independently prognostic in estrogen receptor-negative breast cancer"; Cancer Research, vol. 71, Issue 8, Supplement 1; Apr. 15, 2011.

International Search Report for International Application No. PCT/US2014/010724 mailed Jul. 22, 2014.

Written Opinion International Application No. PCT/US2014/010724 mailed Jul. 22, 2014.

Hebbard, L. et al.; "Maternal Embryonic Leucine Zipper Kinase is Upregulated and Required in Mammary Tumor-Initiating Cells in vivo"; Cancer Research, vol. 70, No. 21; Nov. 2010; pp. 8863-8873.

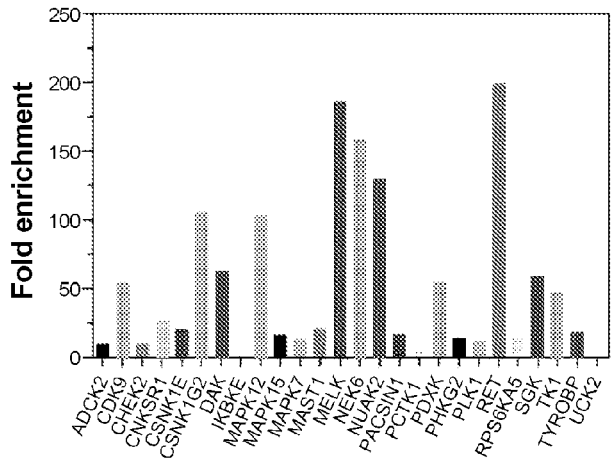

B

| Gene | Description |
|---|---|
| ADCK2 | aarF domain containing kinase 2 |
| CDK9 | cyclin-dependent kinase 9 |
| CHEK2 | checkpoint kinase 2 |
| CNKSR1 | connector enhancer of kinase suppressor of Ras 1 |
| CSNK1E | casein kinase 1, epsilon |
| CSNK1G2 | casein kinase 1, gamma 2 |
| DAK | dihydroxyacetone kinase 2 homolog |
| IKBKE | inhibitor of nuclear factor kappa-B kinase subunit epsilon |
| MAPK12 | mitogen-activated protein kinase 12 |
| MAPK15 | mitogen-activated protein kinase 15 |
| MAPK7 | mitogen-activated protein kinase 7 |
| MAST1 | microtubule associated serine/threonine kinase 11 |
| MELK | maternal embryonic leucine zipper kinase |
| NEK6 | NIMA (never in mitosis gene a)-related kinase 6 |
| NUAK2 | NUAK family, SNF1-like kinase, 2 |
| PACSIN1 | protein kinase C and casein kinase substrate in neurons protein 1 |
| PCTK1 | serine/threonine-protein kinase PCTAIRE-1 |
| PDXK | pyridoxal (pyridoxine, vitamin B6) kinase |
| PHKG2 | phosphorylase kinase, gamma 2 |
| PLK1 | Polo-like kinase 1 |
| RET | "rearranged during transfection" proto-oncogene |
| RPS6KA5 | ribosomal protein S6 kinase alpha-5 |
| SGK | serum/glucocorticoid regulated kinase 1 |
| TK1 | Thymidine kinase 1 |
| TYROBP | TYRO protein tyrosine kinase binding protein |
| UCK2 | uridine-cytidine kinase 2 |

MELK REGULATION FOR THE TREATMENT OF BREAST CANCER

RELATED APPLICATIONS

This application claims the benefit under 35 U.S.C. §371 of International Application No. PCT/US2014/010724, filed Jan. 8, 2014, which claims the benefit of Provisional Application No. 61/751,703, filed Jan. 11, 2013 which are incorporated by reference herein in their entirety.

FEDERALLY SPONSORED RESEARCH OR DEVELOPMENT

This invention was made with government support under federal grant numbers CA134502, P50CA089393-08S1 and CA148164-01 awarded by the National Institutes of Health and federal grant number BC051565 awarded by the Department of Defense. The government has certain rights in the invention.

BACKGROUND OF THE INVENTION

Breast cancer is a heterogeneous disease with a high degree of diversity in histology, therapeutic response, and patient treatment outcomes. Transcriptional profiling analyses have reproducibly identified at least five major "intrinsic" subtypes of breast cancer: normal breast-like, luminal A, luminal B, HER2/Neu-enriched, and basal-like breast cancer (BBC) (Perou et al., 2000; Sorlie et al., 2001). These molecular subtypes have recently been confirmed in a comprehensive characterization of human breast tumors at the genomic, epigenetic, transcriptomic, and proteomic levels (Koboldt et al., 2012). Among these subtypes, basal-like breast cancer (BBC) is strongly associated with an aggressive phenotype and poor prognosis (Foulkes et al. 2010; Perou 2011). Unlike their luminal counterparts, BBC cells lack expression of estrogen receptor (ER) and progesterone receptor (PR), and thus largely overlap with the clinically defined "triple-negative" breast cancers (TNBC), which is also characterized by the lack of ER/PR expression (Foulkes et al, 2010; Perou 2011). The lack of these molecular targets renders BBC or TNBC cells relatively unresponsive to targeted therapies that are highly effective in the treatment of luminal breast cancer. Establishing the molecular pathogenesis of this subtype and identifying potential targets for treatment remains a key challenge for BBC/TNBC.

Kinases represent a unique population of genes that are frequently involved in tumor pathogenesis. Indeed, a large number of mutations, alterations in copy number and/or in expression level have been observed in many kinases across multiple types of human cancers. In addition, kinases are also pharmacologically tractable making inhibition of kinase activity, such as via small molecules, a highly effective strategy for cancer treatment (Zhang et al., 2009). Accordingly, there remains a need for identification of kinase(s) critical for ER/PR expression negative cells in a manner that elucidates "druggable" targets for effective long-term treatment strategies for ER/PR expression negative breast cancers, for new methods of identifying patients that are likely to benefit from the treatment strategies, and for methods of treating patients with the effective long-term treatment strategies.

SUMMARY OF THE INVENTION

The present invention is directed to methods for inhibiting growth or proliferation of breast cancer cells. The methods include administering to a subject in need thereof in an amount that is effective to inhibit growth or proliferation of the breast cancer cells a MELK inhibitor, wherein the breast cancer cells are estrogen receptor (ER) negative. In some aspects, the methods include administering to a subject in need thereof in an amount that is effective to inhibit growth or proliferation of the breast cancer cells a FoxM1 inhibitor, wherein the breast cancer cells are estrogen receptor (ER) negative. In some aspects, the methods include administering to a subject in need thereof in an amount that is effective to inhibit growth or proliferation of the breast cancer cells a MELK inhibitor, a FoxM1 inhibitor or a MELK inhibitor and a FoxM1 inhibitor, wherein the breast cancer cells are estrogen receptor (ER) negative.

The present invention is also directed to methods for treating a subject having breast cancer. The methods include determining an estrogen receptor expression status in breast cancer cells of the subject and administering a MELK inhibitor to the subject having breast cancer cells that are estrogen receptor (ER) negative. In some aspects, the methods include determining an estrogen receptor expression status in breast cancer cells of the subject and administering a FoxM1 inhibitor to the subject having breast cancer cells that are estrogen receptor (ER) negative. In some aspects, the methods include determining an estrogen receptor expression status in breast cancer cells of the subject and administering a MELK inhibitor, a FoxM1 inhibitor or a MELK inhibitor and a FoxM1 inhibitor to the subject having breast cancer cells that are estrogen receptor (ER) negative.

Another aspect of the present invention includes a method of identifying subjects having cancer likely to benefit from a treatment with a MELK inhibitor, a FoxM1 inhibitor or a MELK inhibitor and a FoxM1 inhibitor. The method includes determining an estrogen receptor expression status in breast cancer cells of the subject and/or determining a MELK expression level in the breast cancer cells relative to non-breast cancer cells. The method also includes identifying the subject having breast cancer cells that are estrogen receptor negative and/or that have a greater expression level of MELK in the breast cancer cells relative to non-breast cancer cells. In some aspects, the subject having estrogen receptor negative breast cancer cells and/or a greater level of MELK expression indicates a need to treat the subject with a MELK inhibitor. In some aspects, the subject having estrogen receptor negative breast cancer cells and/or a greater level of MELK expression indicates a need to treat the subject with a FoxM1 inhibitor. In some aspects, the subject having estrogen receptor negative breast cancer cells and/or a greater level of MELK expression indicates a need to treat the subject with a MELK inhibitor, a FoxM1 inhibitor or a MELK inhibitor and a FoxM1 inhibitor.

(A) Development of an in vivo tumorgenesis model. The number of tumors formed and the number of injections were described in the left table. Note that in human mammary epithelial cells (HMECs), two oncogenes were required for cells to achieve tumorigenesis in vivo. The right image of mice showing tumors formed in HMEC-DD-NeuT cells transduced with PIK3CA (H1047R). (B) Schematic of genetic screen for genes that promote tumor formation. A pool of retroviral of myristoylated kinase (37 pool total, each consisting of 10-12 unique open reading frames) was transduced into HMED-DD-ErbB2 cells. Cells were then transplanted into mammary fat pads of nude mice. Tumors generated from 12 pools of cells were harvested followed by the extraction of genomic DNA. Genomic DNA from cells before transplantation and from tumors was subjected to qPCR. The relative enrichment was derived from the differences of Ct numbers. Among twenty-six genes identified, MELK is highly enriched in the developed tumor.

FIG. 2 illustrates twenty-six kinases that were specifically enriched during the development of tumors. (A) List of screen hits and their relative fold enrichment in the in vivo tumors. The threshold for fold enrichment is set to 10. (B) List of screen hits and their gene description.

Figure 3:
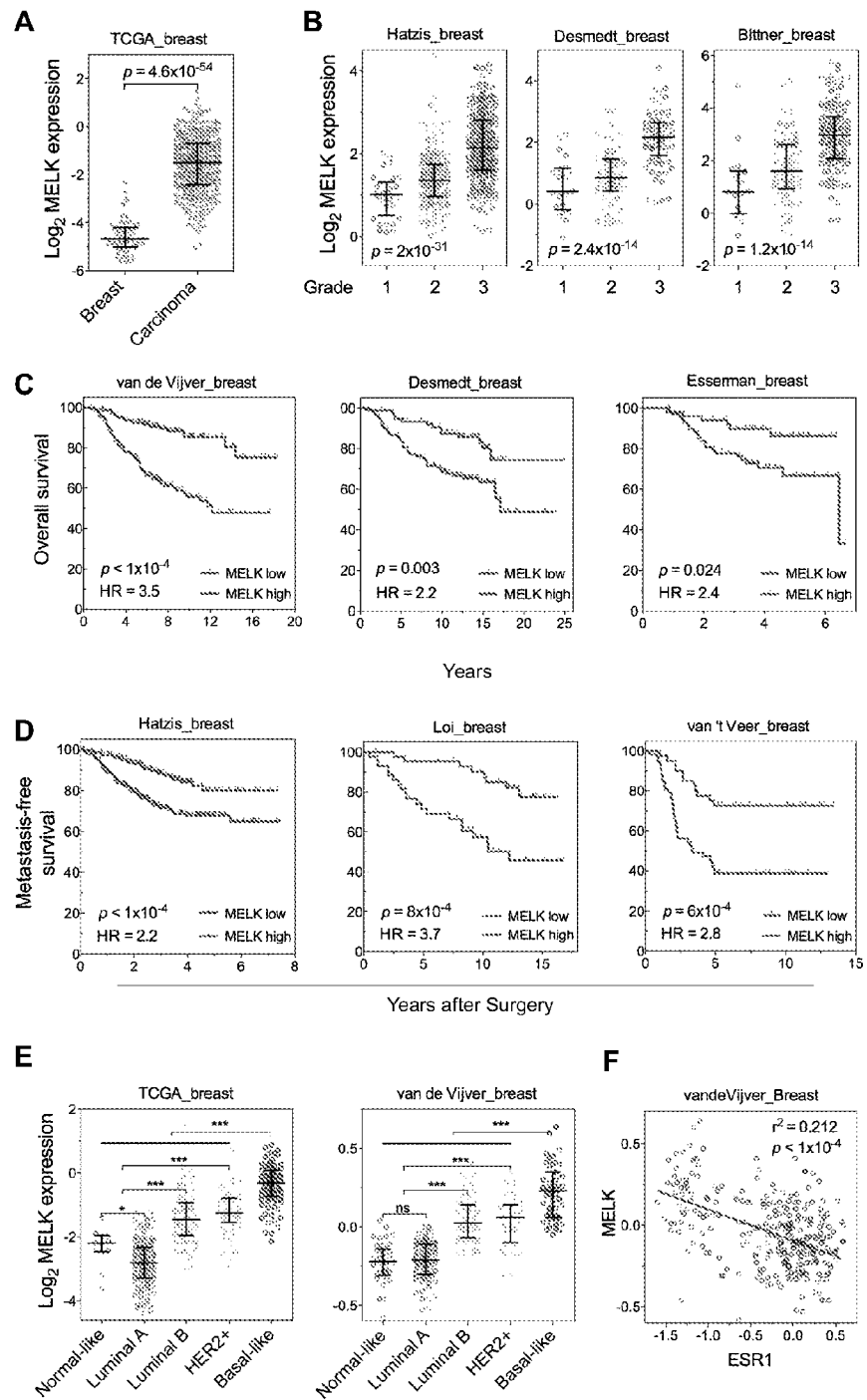

FIG. 3 illustrates that MELK is a top-ranking overexpressed gene in breast cancer and has remarkable prognostic value.

(A) MELK is overexpressed in breast cancer. MELK expression was analyzed between normal breasts (n=61) and invasive ductal breast carcinoma (n=392) in a TCGA breast cancer cohort (Koboldt et al., 2012). Each circle represents an individual sample. Black lines in each group indicate median with interquartile range. P value was obtained from two-tailed Student's t-test. Note that the p value for MELK overexpression in malignant relative to normal breasts ranks 29th among those of the total 20,423 genes measured. (B) MELK expression correlates with the histologic grade of breast cancer. The expression of MELK was compared among breast tumors of different histologic grade. Black lines in each group indicate median with interquartile range. P value was calculated with one-way analysis of variance (ANOVA). Note that the p value for the correlation between MELK expression and the grade of disease ranks $3^{rd}$ (Hatzis cohort) and $8^{th}$ (Desmedt cohort) among those of the total 12,624 genes measured, and $7^{th}$ (Bittner cohort) among those of the total 19,574 genes measured. (C) Kaplan-Meier analysis of overall survival in three independent breast cancer patient cohorts. Samples were divided into two groups, those with high (top 60%) and those with low (bottom 40%) expression of MELK. P values were obtained from Log-rank test, hazard ratio (HR) was calculated using GraphPad Prism version. (D) Kaplan-Meier analysis of metastasis-free survival in three independent breast cancer patient cohorts. Samples were divided as in (C). Log-rank p values and hazard ratios (HR) are shown. (E) Highest expression of MELK in basal-like breast cancer. Samples in each cohort were classified into five distinct molecular subtypes using PAM50 (Parker et al., 2009). Black lines in each group indicate median with interquartile range. ***p<0.0001. *p<0.05. (F) Inverse correlation between the expression of MELK and that of estrogen receptor (ER, or ESR1). Each circle represents one individual human breast tumor sample (n=295). Correlation analysis was performed by GraphPad Prism. All the gene expression data were downloaded from Oncomine (Rhodes et al., 2004), and were analyzed. The original articles for the cited data sets are listed in Table S1 below.

Figure 4:
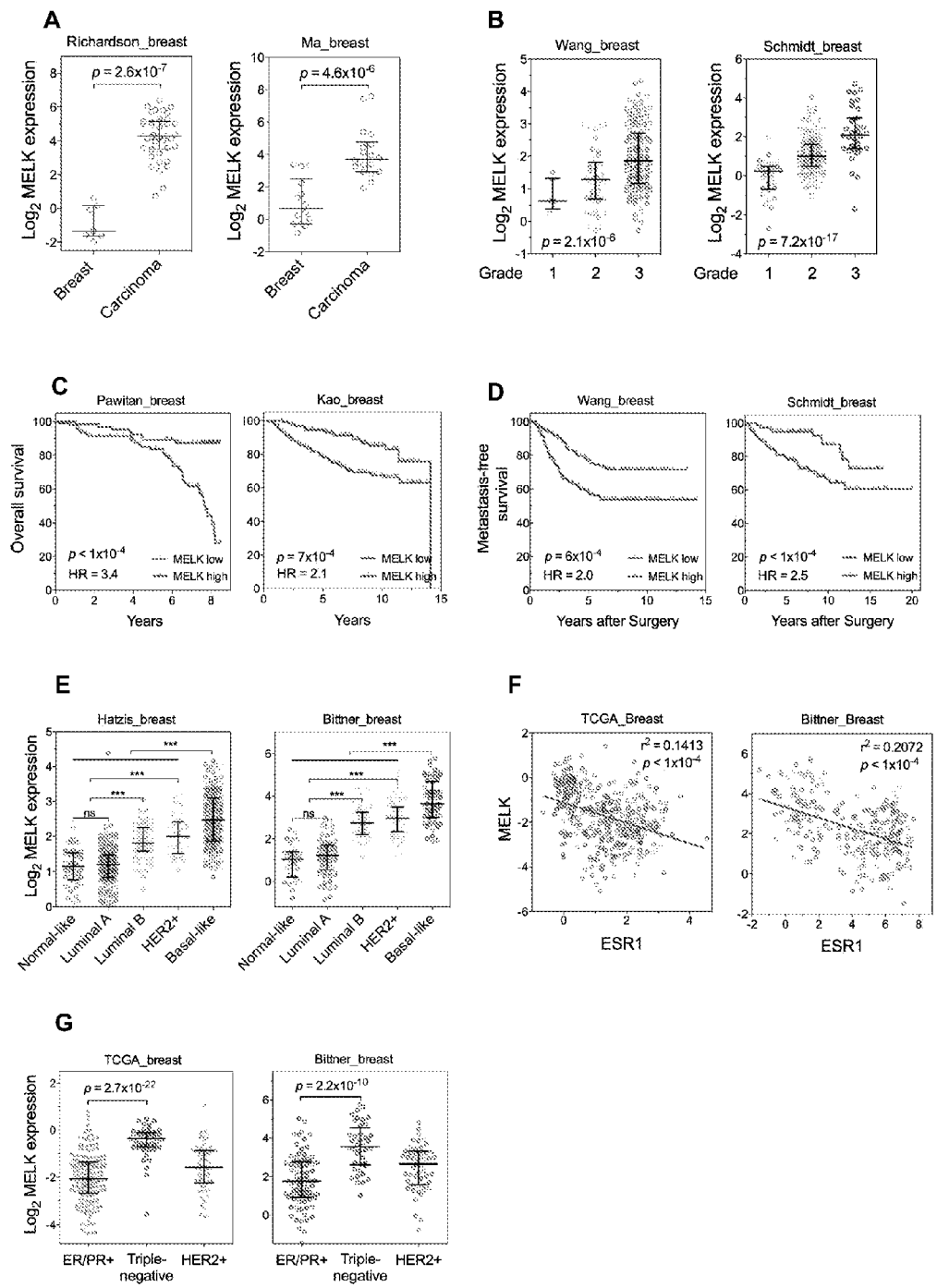

FIG. 4 illustrates that MELK is a top-ranking overexpressed gene in breast cancer and has strong prognostic value (A) MELK expresses at a higher level in breast tumors than in normal breast tissues. (B) MELK expression is positively correlated with the histologic grade of disease. The indicated p values rank 7th (of total 19,574 genes measured, Bittner cohort) and 3rd (of total 12,624 genes measured, Hatzis cohort). (C) MELK expression predicts metastasis. Samples in the indicated cohorts were divided into groups of MELK high and MELK low, which represent the top 60% and bottom 40% in the descending order of MELK expression. Kaplan-Meier curves are shown, with log-rank p values and hazard ratios (HR). (D) High MELK expression predicts inferior overall survival of breast cancer patients. Samples were grouped into MELK high and low as in (D). P values were obtained from log-rank test, hazard ratio (HR) was calculated using GraphPad Prism. (E) MELK expression in subtypes of breast cancer that are defined by gene expression profiling. Samples were divided into subtypes based on PAM50 gene signature (Parker et al., 2009). "ns" denotes not significant. "****" p<0.0001. (F) Inverse correlation between the expression of MELK and that of estrogen receptor (ER, or ESR1). (G) Triple-negative breast cancer exhibits higher expression of MELK than other subtypes. Patients were classified into groups with subtypes of diseases based on expression of estrogen receptor (ER), progesterone receptor (PR), or human epidermal growth factor 2 (HER2). All the data were downloaded from Oncomine (Rhodes et al., 2004), and were re-analyzed. The black lines in each panel (A, B, E, F) indicate median with interquartile range.

Figure 5:
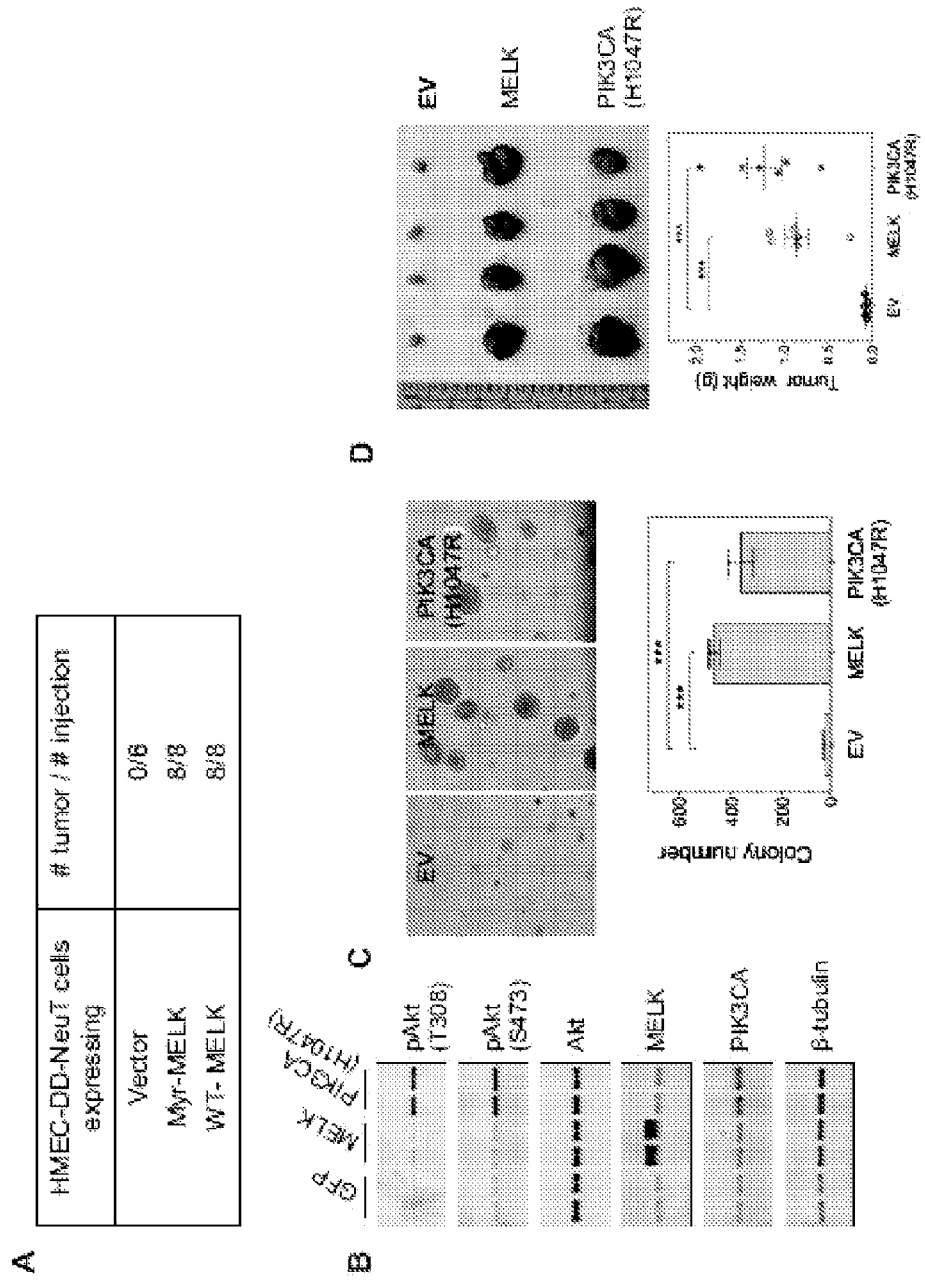
Figure 5:
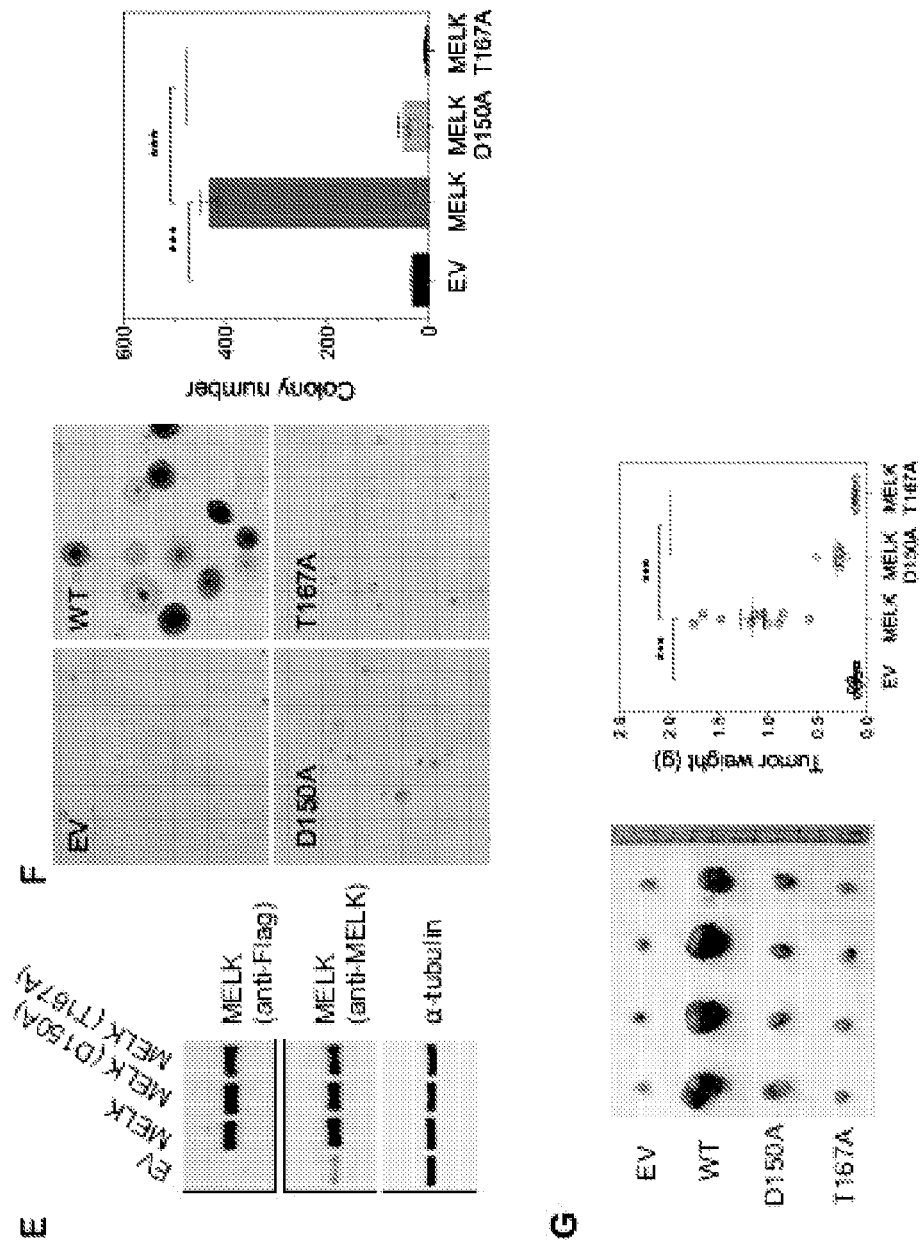

FIG. 5 illustrates that MELK overexpression confers tumorigenic potential.

(A) Wildtype MELK, when overexpressed, is oncogenic. HMEC-DD-NeuT cells were transduced with empty vector, myristoylated or wildtype MELK. Cells were transplanted into mammary fat pads of nude mice. The number of tumors formed and the number of injections were described in the table. (B) Overexpression of MELK in Rat1-DD-TP53 cells. The cells were stably introduced with GFP (as a negative control), or wildtype human MELK, or an oncogenic allele of p110α (H1047R). The ectopic expression of these genes is driven by the long terminal repeat of Moloney murine leukemia virus. Note that expression of p110α (H1047R) enhances Akt phosphorylation. β-tubulin serves as a loading control. (C) Colony formation assay in soft agar. The indicated cells were seeded in 12-well plate at the density of 4000 cell per well. The plates were harvested after 3 weeks. The top panel shows representative bright-field images of the colonies. The bottom indicates quantitative analysis of colony formation, which is shown as the total number of colonies per well. EV denotes empty vector. *p<0.001. (D) MELK overexpression drives tumor formation. The indicated cells were transplanted to immunocompromised mice, and subcutaneous tumors were harvested after three weeks. The top and bottom panel respectively indicate the images of tumors and the quantification of tumor weight. *p<0.001. (E) Overexpression of wildtype and kinase-inactive MELK in Rat1-DD-TP53 cells. Cells were stably introduced with pWzl empty vector (EV) or pWzl harboring Flag-tagged MELK, which express human MELK driven by the long terminal repeat of Moloney murine leukemia virus. (F) Overexpression of kinase-inactive MELK does not confer anchorage-independent cell growth. Colony formation assays were done as in (C). The left and right panels show the representative bright-field images of the colonies and the quantitative analysis respectively. *p<0.001. (G) Overexpression of catalytically inactive MELK does not induce tumor growth. Subcutaneous xenografts were performed as in (E). The left and right panel show tumor pictures and quantification of tumor weight respectively. *p<0.001.

Figure 6:
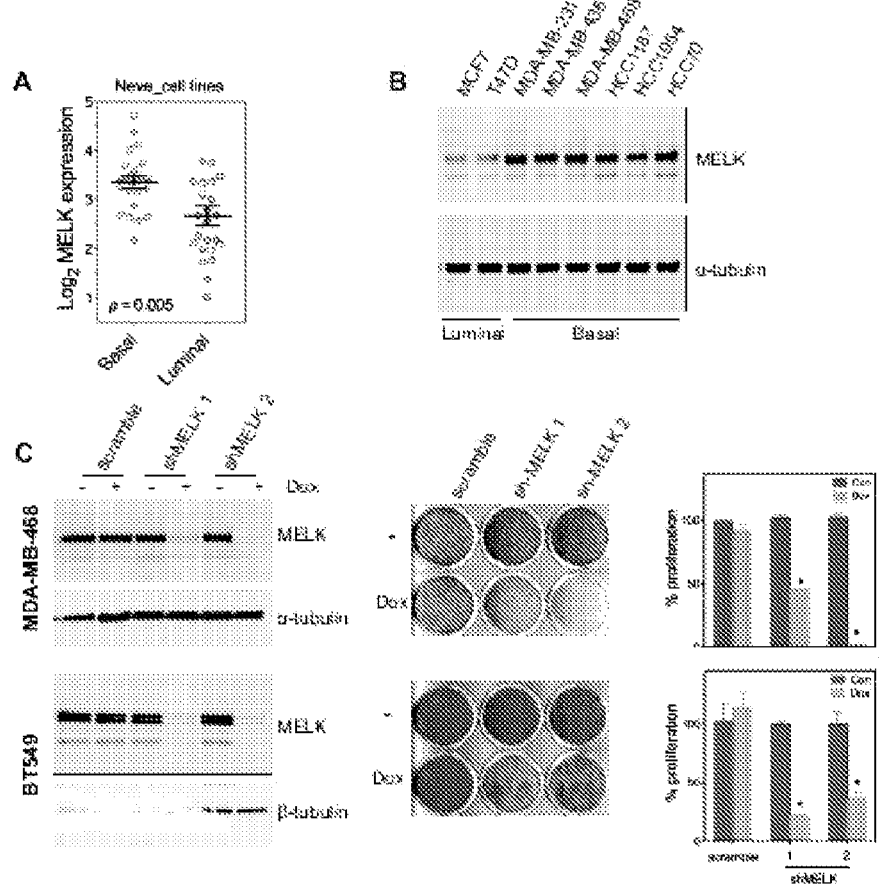
Figure 6:
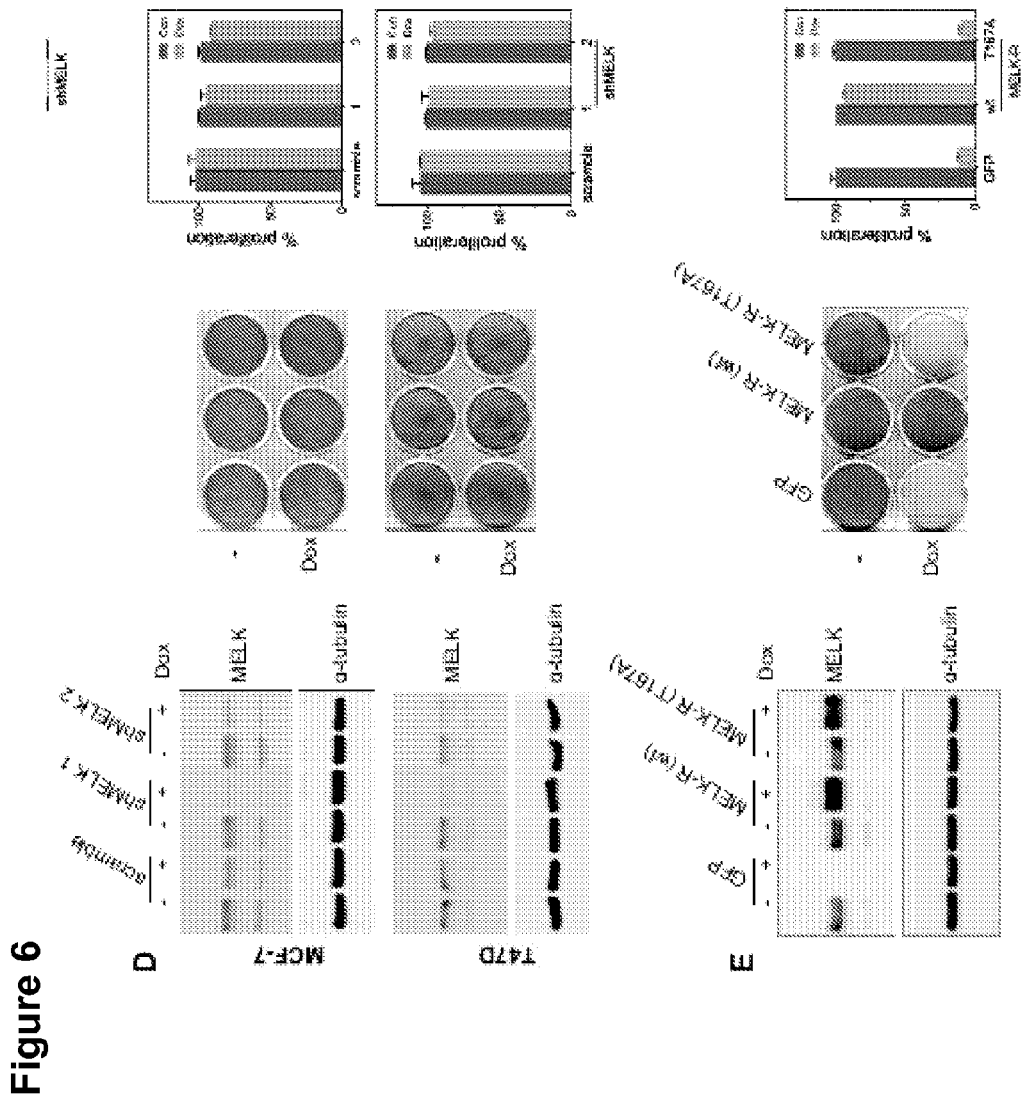

FIG. 6 demonstrates that MELK is necessary for the proliferation of basal-like breast cancer cells.

(A) Basal breast cancer cell lines have higher expression levels of MELK than luminal cancer cells. The MELK mRNA data among 16 established basal and 20 luminal breast cancer cell lines were from the Neve dataset (Neve et al., 2006). The black line of each group represents mean±SEM. P value was calculated by Student's t-test. (B) Protein abundance of MELK is higher in basal than in luminal breast cancer cells. Lysates from the indicated cells were subjected to immunoblotting. α-tubulin was used a loading control. (C) Conditionally knocking down MELK in two basal breast cancer cell lines (MDA-MB-468, BT-549) suppresses MELK expression and inhibits cell proliferation. The left panels of immunoblotting indicate MELK expression in cells untreated or treated with doxycycline (Dox, 100 ng/ml) for three days. The middle and the right panels show respectively the crystal violet staining of the plates and the quantification of the staining. The error bars indicate standard deviation. "*" denotes p value <0.001. (D) Conditionally knocking down MELK in two luminal breast cancer cell lines (MCF-7, T47D) inhibits MELK expression but exerts little effect on cell proliferation. The panels are arranged as in (C). *p<0.001. (E) Expression of shMELK-resistant MELK rescues the phenotypes induced by MELK silencing. MDA-MB-468 cell with stable tet-on-shMELK were stably introduced with a tetracycline-inducible gene expression vector encoding GFP, or wildtype shMELK-resistant MELK, or kinase-inactive shMELK-resistant MELK. Note that the exogenous MELK is tagged with Flag, causing a slight shift of MELK on the protein gel. The left, middle, and right panels show respectively immunoblotting, crystal violet staining, and quantitative analysis of cell proliferation.

Figure 7:
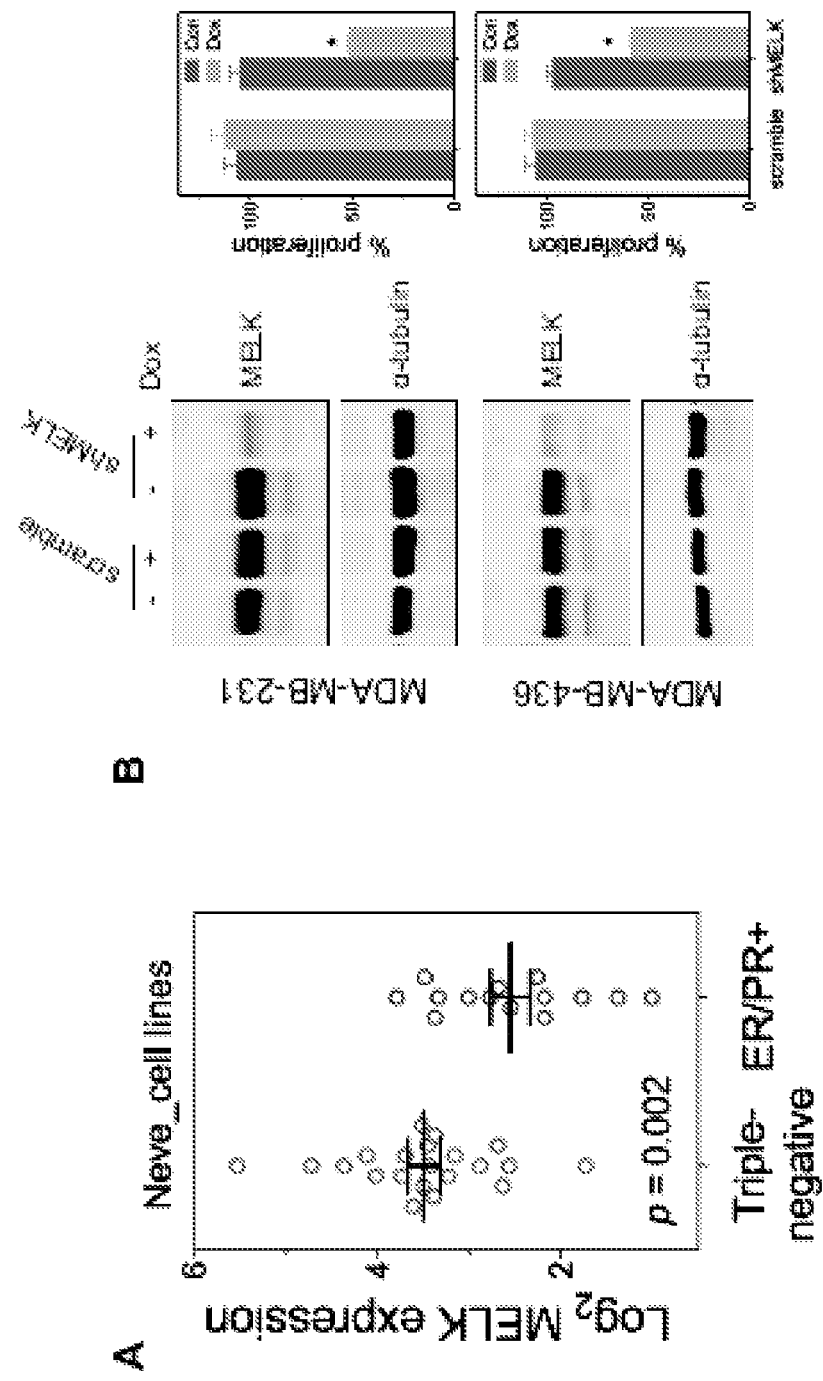
Figure 7:
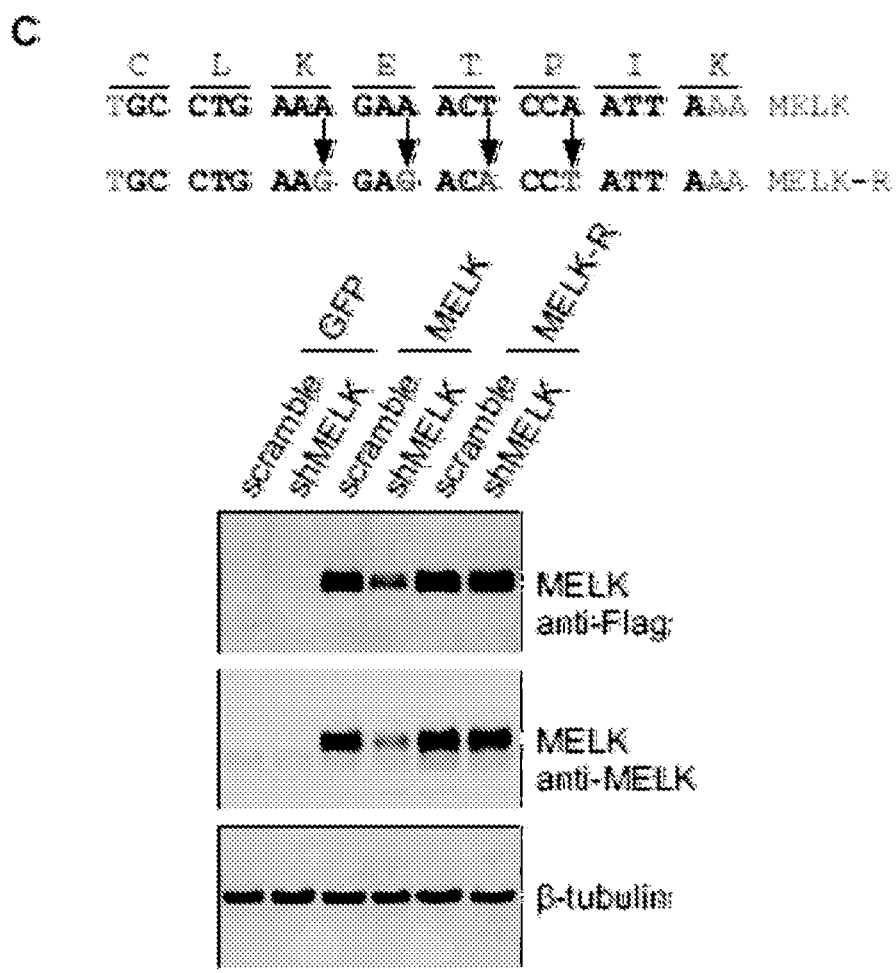

FIG. 7 demonstrates that MELK is necessary for the proliferation of basal-like breast cancer cells.

(A) Triple-negative breast cancer cell lines have higher level of MELK than ER/PR+ breast cancer cells. The MELK mRNA data among 21 established triple negative and 14 ER/PR+ breast cancer cell lines were obtained from the Neve dataset (Neve et al., 2006). The black line of each group represents mean±SEM. P value was calculated by Student's t-test. (B) Conditionally knocking down MELK in two additional BBC cell lines suppresses cell proliferation. Left panels of immunoblotting indicate MELK expression in cells exposed to doxycycline (100 ng/ml) for three days. Right panels represent quantification of cell proliferation, with error bars indicating standard deviation. *p<0.05, **p<0.01. (C) Generation of shMELK-resistant MELK cDNA (MELK-R). Top, the 21-mer sequence targeted by shMELK2 is marked in bold. The silent mutations are indicated by the arrows. Bottom, the indicated shRNA (scramble or shMELK) were co-transfected with plasmid encoding GFP, or parental MELK, or MELK-R. Cell lysates were harvested for immuoblotting. Note that MELK-R, but not the parental wild type MELK is resistant to shMELK.

Figure 8:
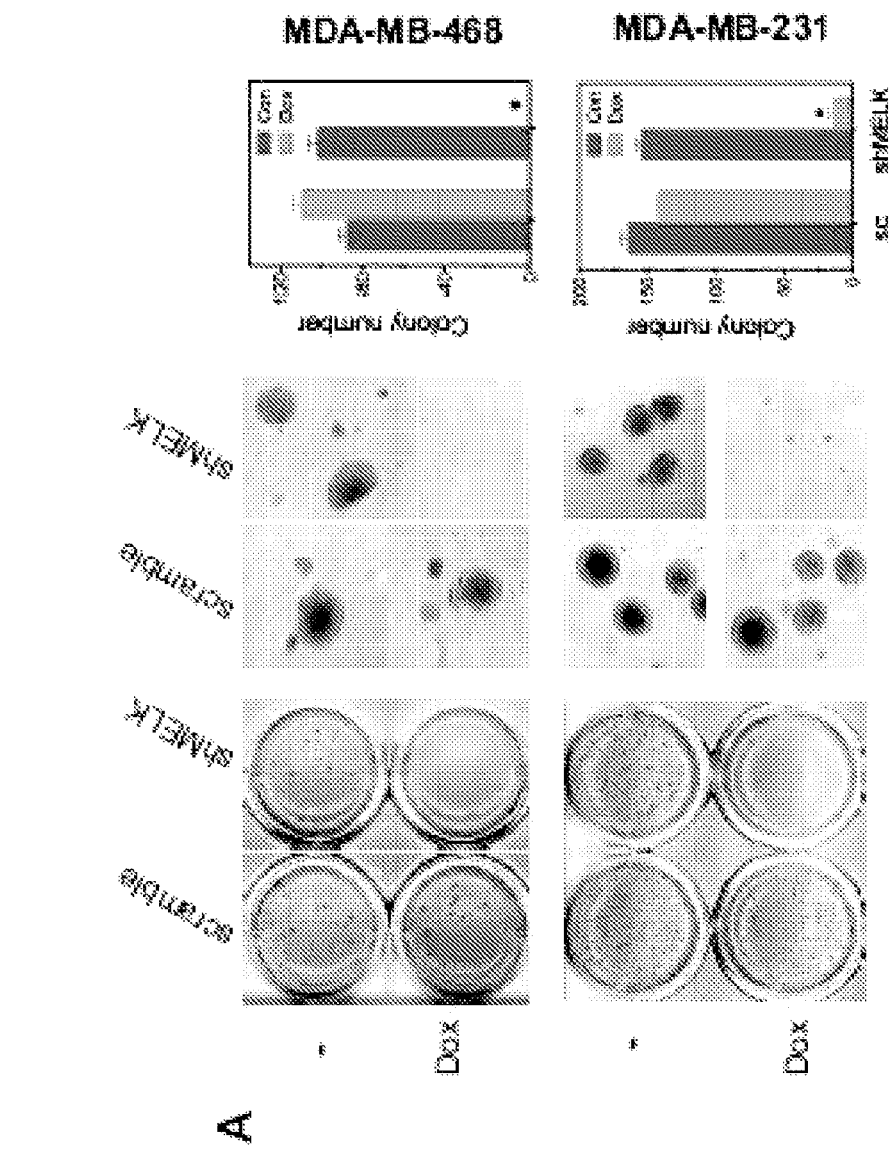
Figure 8:
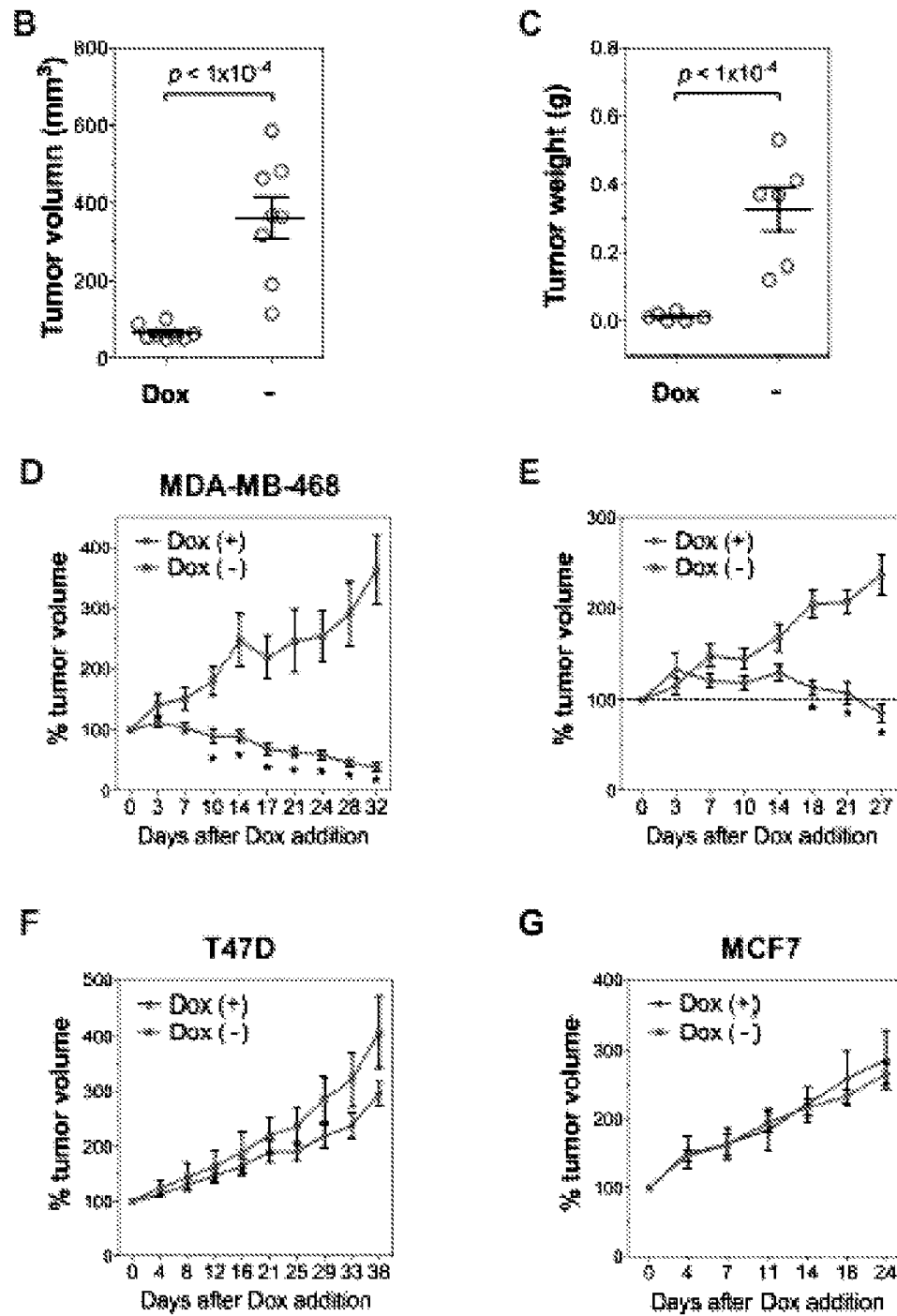

FIG. 8 illustrates that MELK is necessary for the malignant growth of basal-like breast cancer cells.

(A) MELK knockdown suppresses anchorage-dependent cell growth. The indicated cells were seeded in 0.3% agar, and treated without or with 100 ng/ml doxycycline. The left and middle panels show respectively crystal violet staining of the colonies and bright-field images of the colonies. The right panel indicates the number of colonies per well of a 12-well plate. Error bars represent standard deviation. *p<0.001. (B, C) Conditionally knocking down MELK impairs tumor growth. MDA-MB-468 (B) or MDA-MB-231 cells (C) with stable tet-on-shMELK were orthotopically implanted into the mammary fat pads of nude mice. Half of the mice were given doxycycline-supplemented drinking water from the second day of injection. The histogram indicates tumor volume or weight measured seven weeks after treatment. Error bars represent standard error. (D-G) Knocking down MELK in established tumors impairs tumor growth and trigger regression in basal (MDA-MB-468, MDA-MB-231) but not luminal tumors (T47D, MCF-7). The indicated cells were implanted into the mammary fat pads of mice. When tumors grew into the average size of 200 mm$^3$, mice were randomly divided into two groups, with one group receiving doxycycline. Tumor sizes were measure on the indicated days after treatments. * denotes p<0.001. Error bars represent standard error.

Figure 9:
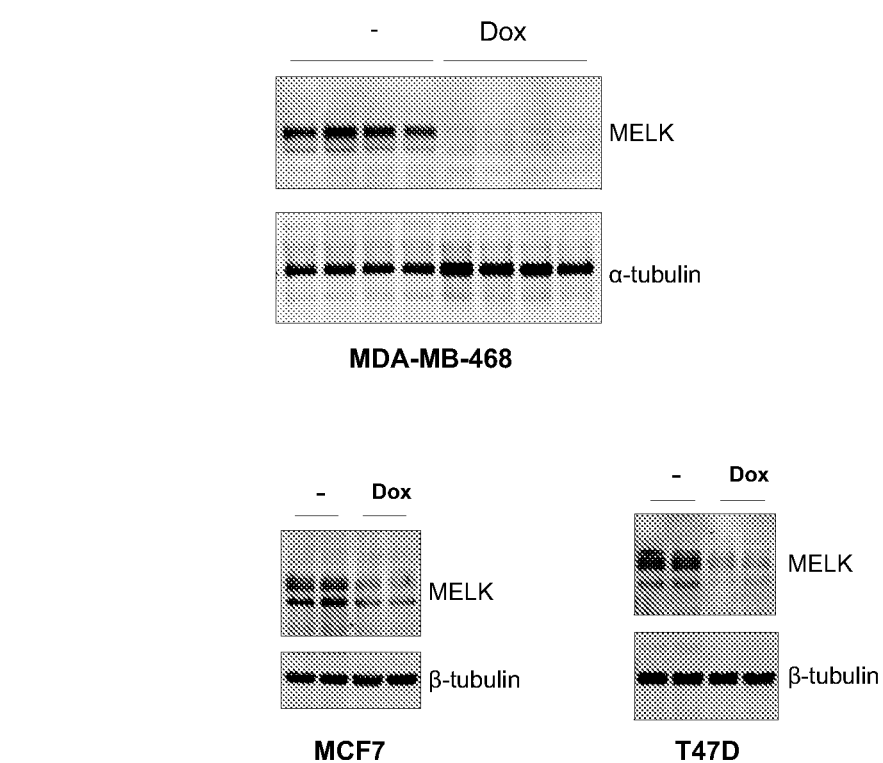

FIG. 9 illustrates that MELK is necessary for the malignant growth of basal-like breast cancer cells.

Mice with mammary tumors derived from the indicated cells with stable tet-shMELK were untreated or treated with doxycycline-supplemented water for four days. Tumors lysates were used for immunoblotting, with α- or β-tubulin served as a loading control.

Figure 10:
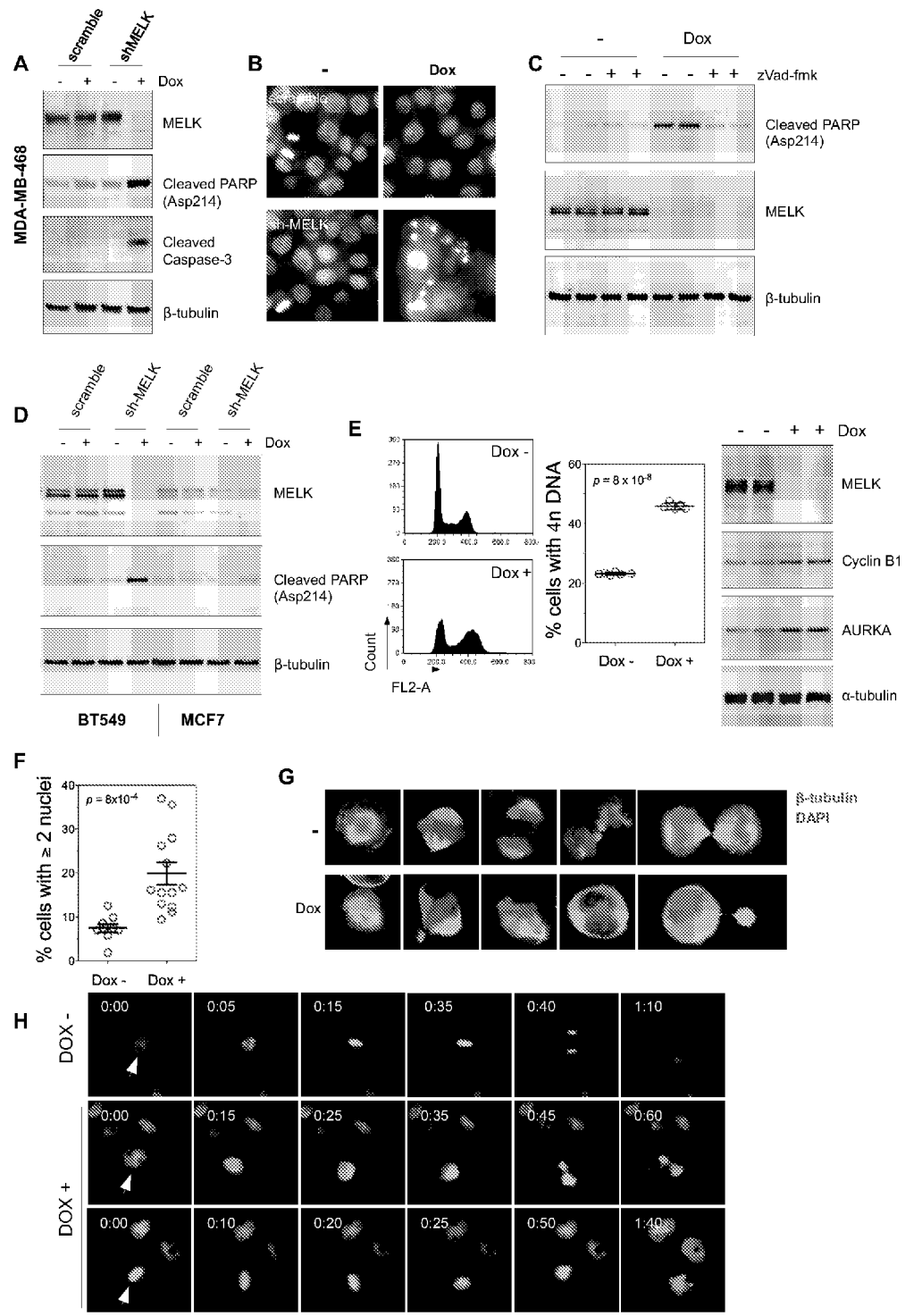

FIG. 10 illustrates that MELK inhibition causes cell death and impaired mitosis.

(A) Immunoblotting assay reveals apoptosis markers induced by MELK inhibition. The indicated cells were left untreated or treated with 100 ng/ml doxycycline for four days. Cell lysates were prepared and subjected to immunoblotting using the indicated antibodies. (B) MELK inhibition induces DNA fragmentation. MDA-MB-468 cells with the indicated stable shRNA were treated as in (A) followed by fixation and staining with DAPI. Note that the bright and particle-like staining indicates DNA fragmentation. (C) MELK inhibition causes caspase-dependent cell death. MDA-MB-468 cells with shMELK were either untreated or treated with 100 ng/ml doxycycline for 4 days, with the last two days with 40 μM zVad-fmk or vehicle. Lysates were prepared for immunoblotting, with β-tubulin as a loading control. (D) MELK inhibition induces cell death selectively in basal breast cancer cells. The indicated cells were left untreated or treated with doxycycline for four days before cell lysates were prepared for immunoblotting. Note that MELK silencing induces the appearance of apoptotic marker (cleaved PARP) in BT549 but not in MCF7 cells. (E) MELK inhibition induces the accumulation of cells with 4n DNA. MDA-MB-468 cells with shMELK were either untreated or treated with doxycycline for five days. Samples were prepared for cell cycle analysis and for immunoblotting. The left panel shows representative cell cycle distribution; the middle histogram indicates the quantification of % cells with 4n DNA content; and the right panel shows immunoblotting. Note that MELK knockdown induces the accumulation of cells with 4n DNA content, as well as the expression of mitotic markers. (F) Defective cytokinesis induced by MELK inhibition. The cells were left untreated or treated with doxycycline for four days, followed by fixation and DAPI staining. Images were acquired with a 20× object lens. Each circle represents a single randomly selected field (total number of cells counted >500 for each group). The data indicate the percentage of cells with two or more than two nuclei. The black lines indicate median±SEM. (G) MELK inhibition induces pleiotropic defects in mitosis. Fluorescent images were obtained from cells stained with anti-β-tubulin (green) and DAPI (DNA). (H) Time-lapse microscopic analysis. MDA-MB-468 cells with stable shMELK and Histone 2B-GFP were left untreated or treated with doxycycline for three days, and then subjected to time-lapse imaging. Time is given in hours:minutes. The top panel shows control mitotic cells; the middle indicates a cell with two nuclei undergoing cell death; in the bottom frames, a cell fails to progress into anaphase, ending with cell death.

Figure 11:
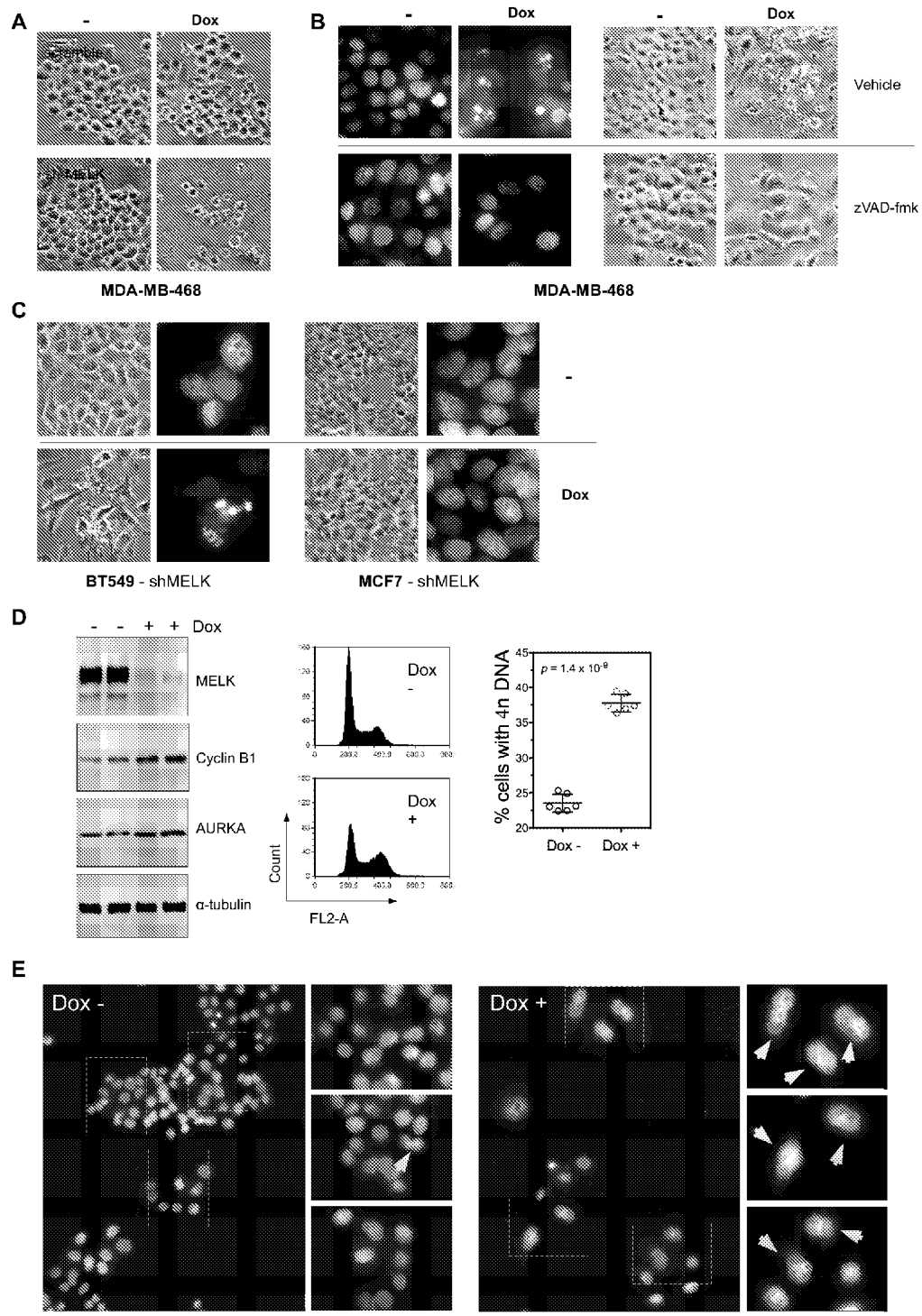

FIG. 11 illustrates that MELK inhibition causes cell death and impaired mitosis.

(A) Bright-field images of indicated cells untreated or treated with doxycycline for the induction of MELK silencing. (B) DAPI staining and bright-field images of MDA-MB-468 cells with tet-shMELK. The cells were untreated or treated with doxycycline for 4 days, and further treated with zVad-fmk or vehicle during the last two days. (C) Conditionally knocking down MELK in BT549 cells induces the accumulation of cells with 4n DNA content and G2/M arrest. BT549 cells with tet shMELK were either treated without or with doxycycline for five days. Cells were subjected to cell cycle analysis by FACS and immunoblotting. The left, middle and right panels show respectively immunoblotting, representative cell cycle distribution histograms, and the quantification of % cells with 4n DNA content. The black lines indicate median±SD. (D) DAPI staining reveals cells with multiple nuclei. MDA-MB-468 cells with tet-shMELK were untreated or treated with doxycycline (100 ng/ml). Arrows indicate cells with two or more nuclei.

Figure 12:
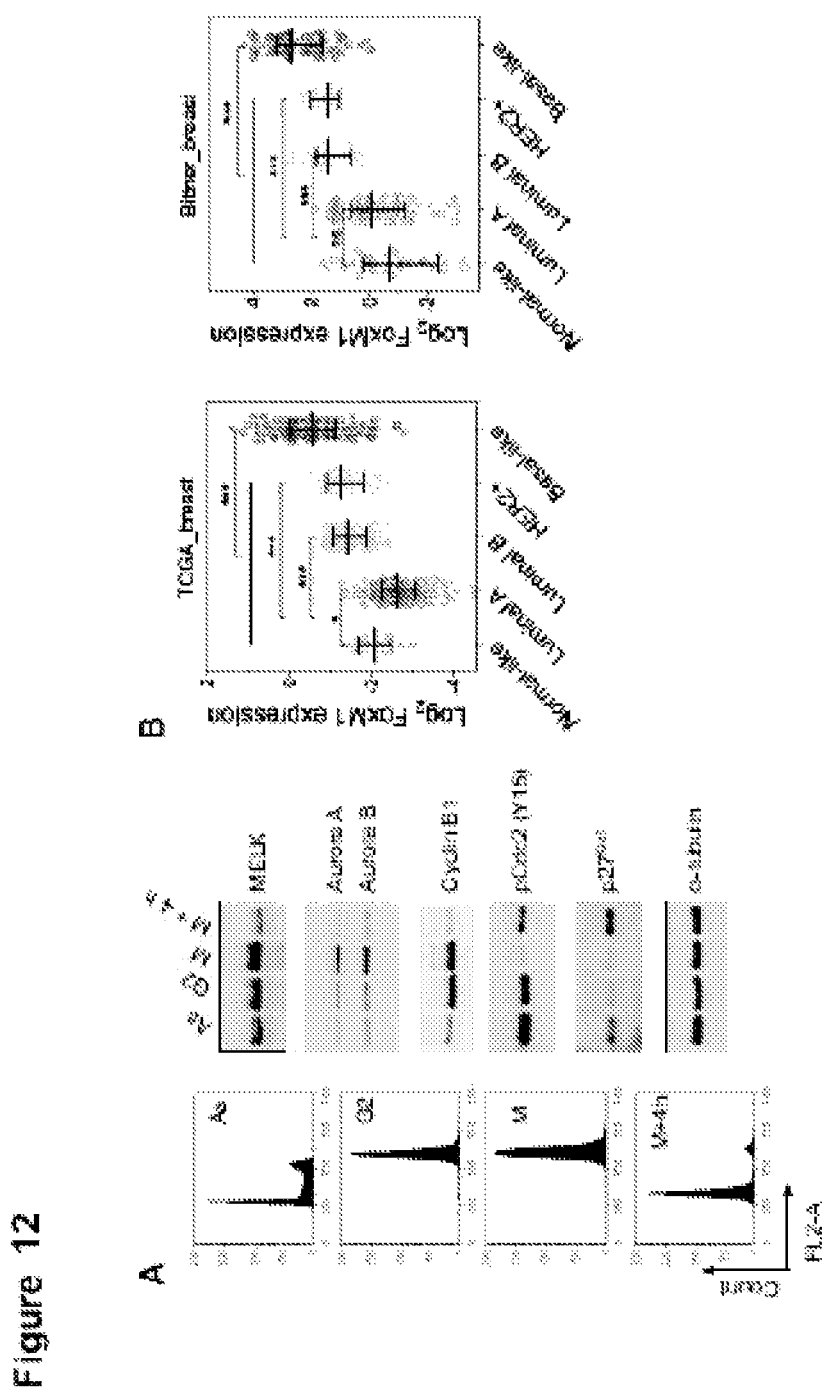
Figure 12:
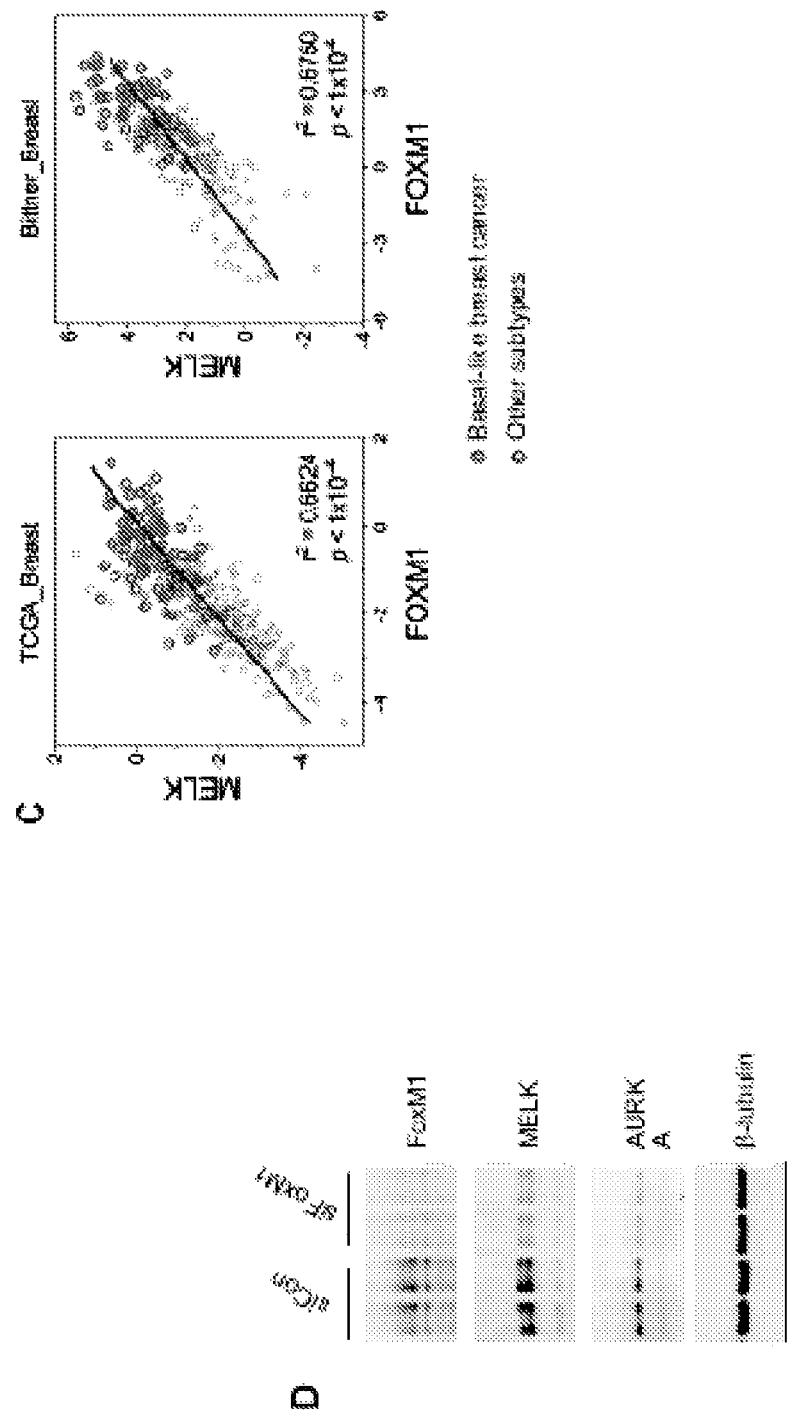
Figure 12:
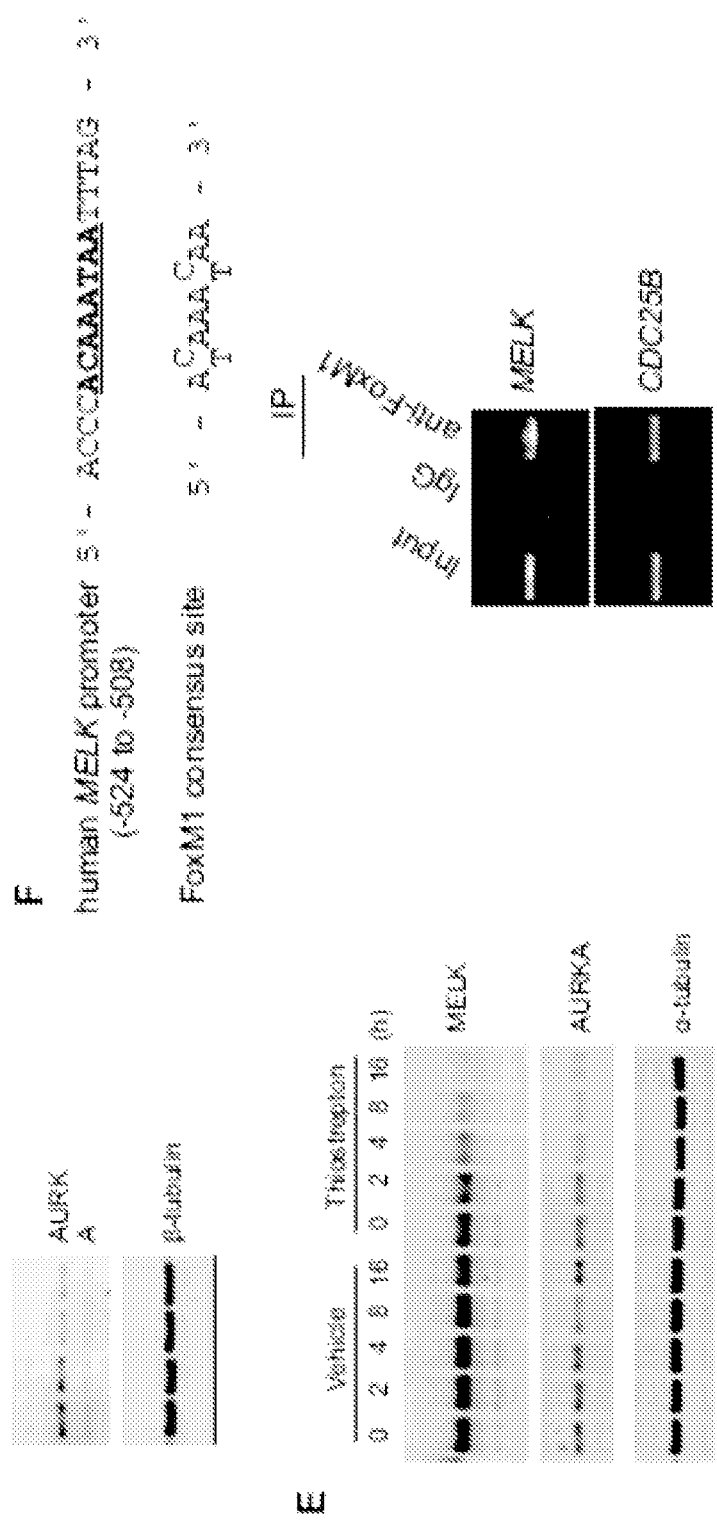

FIG. 12 illustrates that FoxM1 is overexpressed in basal-like breast cancer and regulates the expression of MELK.

(A) Cell cycle-dependent expression of MELK. MDA-MB-231 cells were left untreated (Asynchronized, As) or treated with 100 ng/ml nocodazole for 18 h. Mitotic cells (M) were harvested by shake-off, with the attached cells enriched in G2 phase (G2). A subset of the mitotic cells was washed to remove the nocodazole, and the attached cells (M+4 h) were harvested after 4 hours of incubation. The left and right panels show the FACS analysis of cell cycle and immunoblotting. (B) High expression of FoxM1 in basal-like breast cancer. Samples in the indicated datasets were grouped into subtypes based on PAM50 gene signature (Parker et al., 2009). ***p<0.0001. *p<0.05. (C) FoxM1 and MELK expression are tightly correlated. Expression of MELK was plotted against that of FoxM1. Each circle represents one individual human breast tumor sample (n=349 for TCGA dataset; n=338 for Bittner dataset), with red and green respectively indicating basal-like breast cancer and other subtypes. Correlation analysis was performed by GraphPad Prism. (D) Knocking down FoxM1 suppresses MELK expression. Cells were transfected with either control siRNA or siRNA targeting FoxM1. Lysates were harvested three days after transfection, and were subjected to immunoblotting. Aurora kinase A (AURKA), a known transcriptional target of FoxM1 (Lefebvre et al., 2010), was used as a positive control. (E) FoxM1 inhibition downregulates the expression of MELK. MDA-MB-231 cells were treated for the indicated time with vehicle (0.1% DMSO) or 10 µM thiostrepton, an inhibitor of FoxM1 (Hegde et a., 2011). Protein lysates were prepared for immunoblotting. (F) Top: putative FoxM1 binding site in the MELK promoter. The shown nucleotide sequences are the putative FoxM1 binding site in the MELK promoter (top) and the FoxM1 consensus binding site (bottom). Numbers for the nucleotides are relative to the transcription start site (+1) of MELK. Bottom: Chromatin immunoprecipitation assay of MELK promoter in MDA-MB-468 cells. Control rabbit IgG and antibody against FoxM1 were used. Primers for the promoter region of CDC25B was used a positive control.

Figure 13:
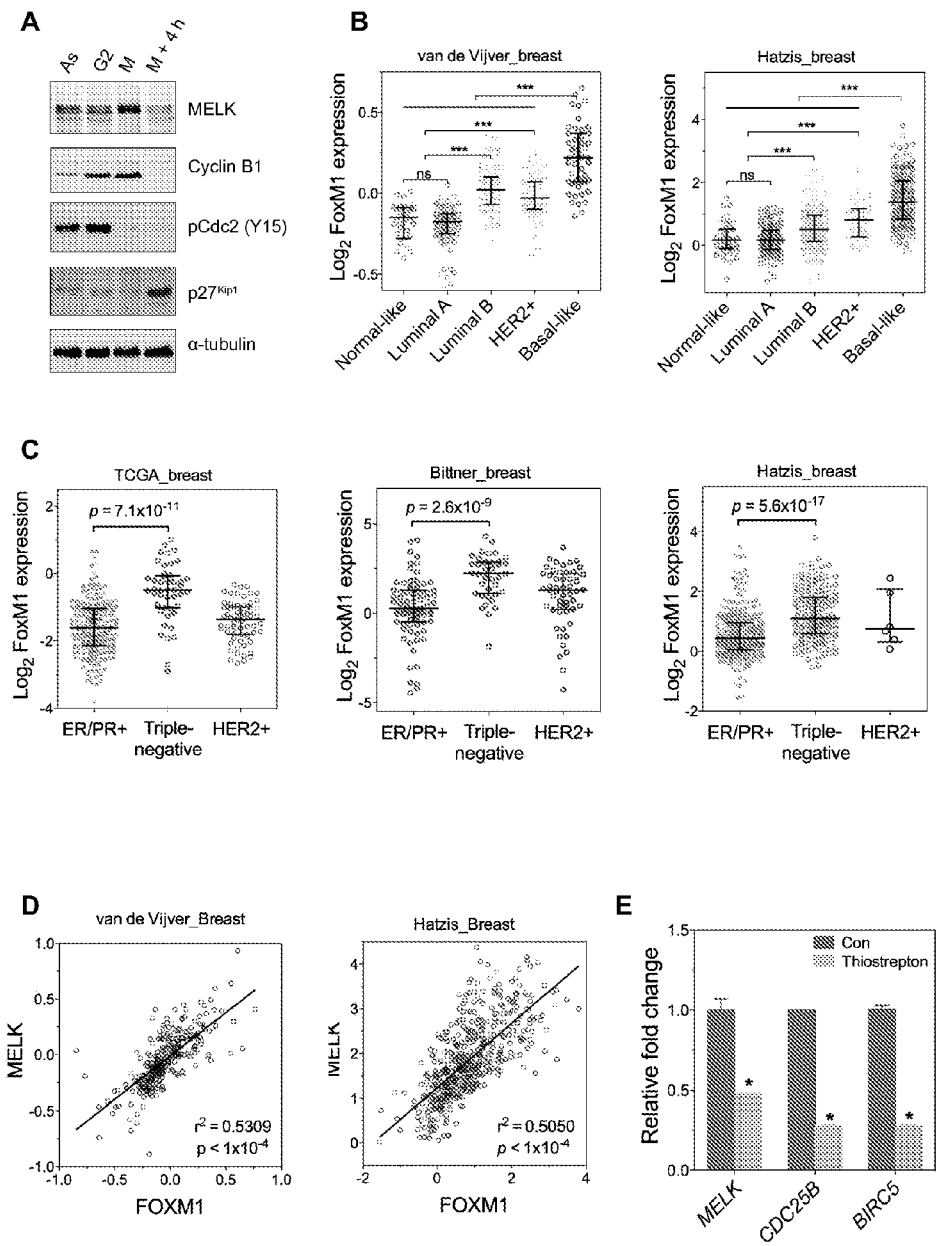

FIG. 13 illustrates that FoxM1 is overexpressed in basal-like breast cancer and regulates the expression of MELK.

(A) Cell cycle-dependent expression of MELK. MDA-MB-468 cells were left untreated (Asynchronized, As) or treated with 100 ng/ml nocodazole for 18 h. Mitotic cells (M) were harvested by shake-off, with the attached cells harvested as those enriched in G2 phase (G2). A part of the mitotic cells was washed off nocodazole, and incubated for four hours before the attached cells (M+4 h) were harvested. Lysates from the prepared cells were prepared and subjected to immunoblotting using the indicated antibodies. (B) FoxM1 expression in subtypes of breast cancer that are defined by gene expression profiling. Samples in the two indicated cohort was grouped into subtypes based on PAM50 gene signature (Parker et al., 2009). "****" denotes p value <0.0001. (C) Expression of FoxM1 is significantly higher in triple-negative breast cancer than in other subtypes. Samples were classified into subtypes based on the protein expression of estrogen receptor (ER), progesterone receptor (PR), or human epidermal growth factor 2 (HER2). The indicated p values were from comparing MELK expression in triple-negative with that in ER/PR+ breast cancer. (D) FoxM1 and MELK expression are tightly correlated. Expression of MELK was plotted against that of FoxM1. Each circle represents an individual human breast tumor sample (n=295 for van de Vijver dataset; n=508 for Hatzis dataset). Correlation analysis was performed by GraphPad Prism. (E) FoxM1 inhibition by thiostrepton decreases the transcription of MELK. Cells were treated with vehicle or thiostrepton for 16 h, and total RNA was extracted followed by cDNA synthesis. Quantitative PCR was performed using the primers for the indicated genes. The error bars indicate standard deviation. "*" denotes p value <0.01.

Figure 14:
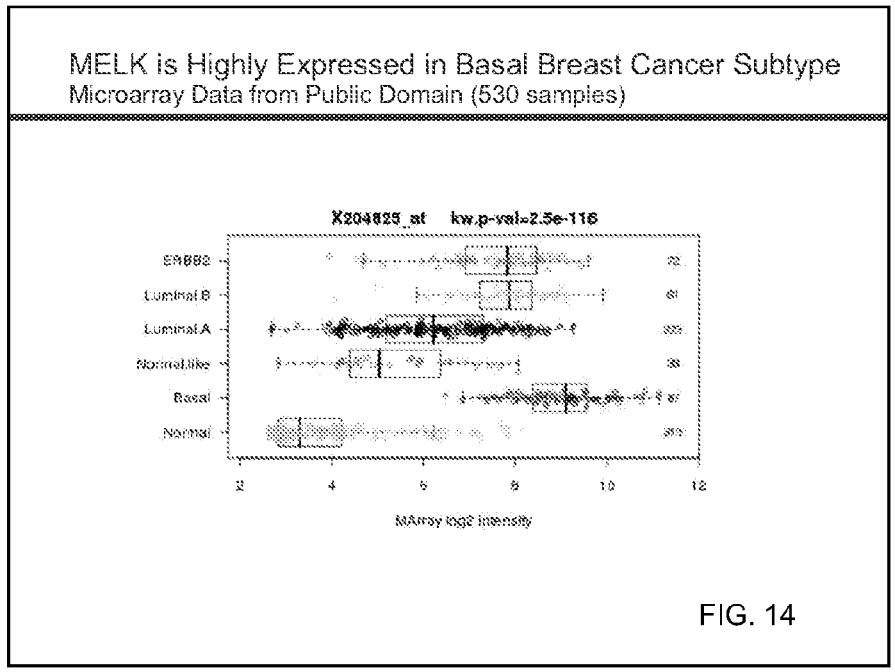

FIG. 14 illustrates that MELK is highly expressed in Basal Breast Cancer subtype.

Figure 15:
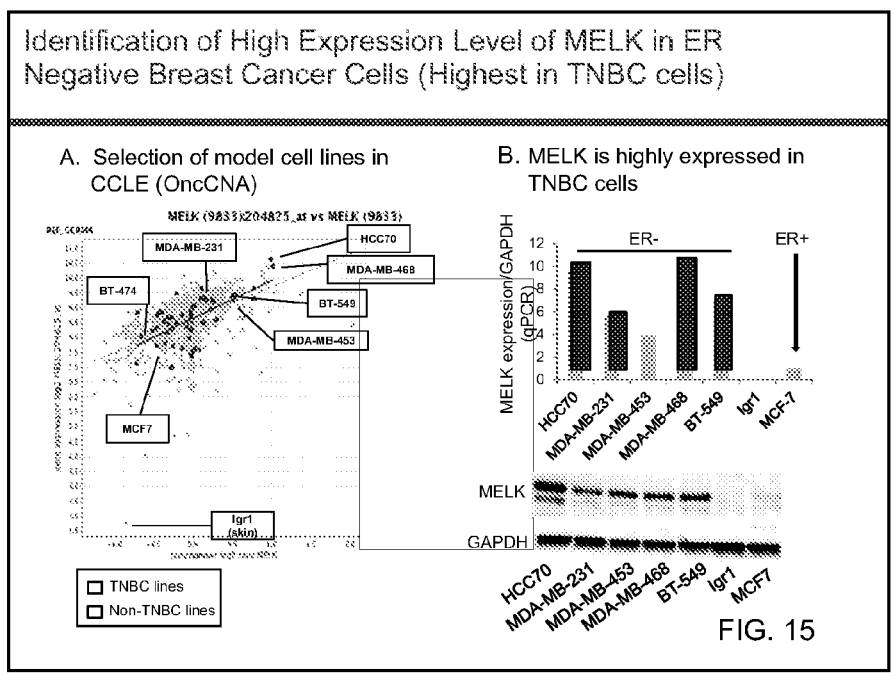

FIG. 15 shows high expression levels of MELK in ER negative breast cancer cells. (A) MELK gene expression in model cell lines. (B) Quantitative PCR showing increased MELK expression in ER− cell lines.

Figure 16:
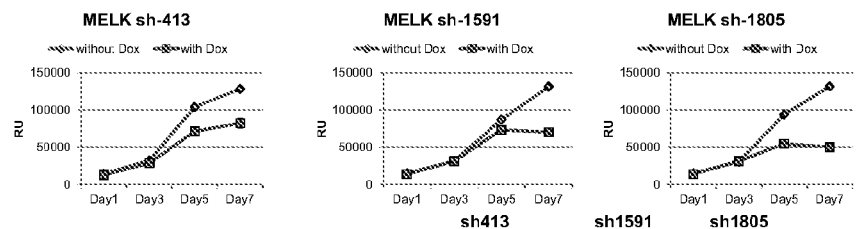

FIG. 16 shows BT549 (ER−, MELK high) breast cancer cells are dependent on MELK.

Figure 17:
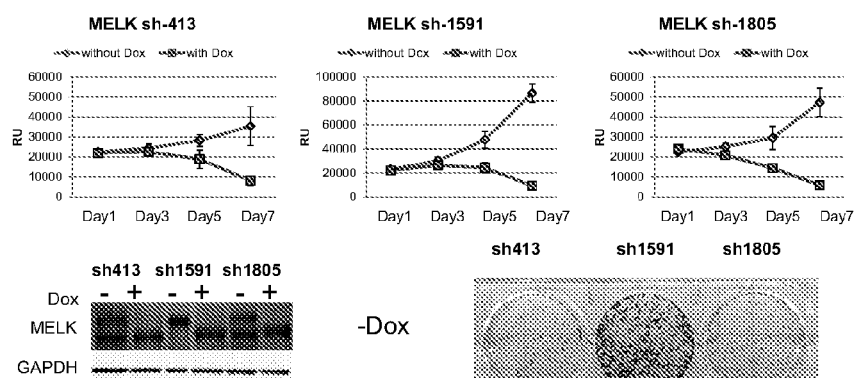

FIG. 17 shows MDA-MB-468 (ER−, MELK high) breast cancer cells are dependent on MELK.

Figure 18:
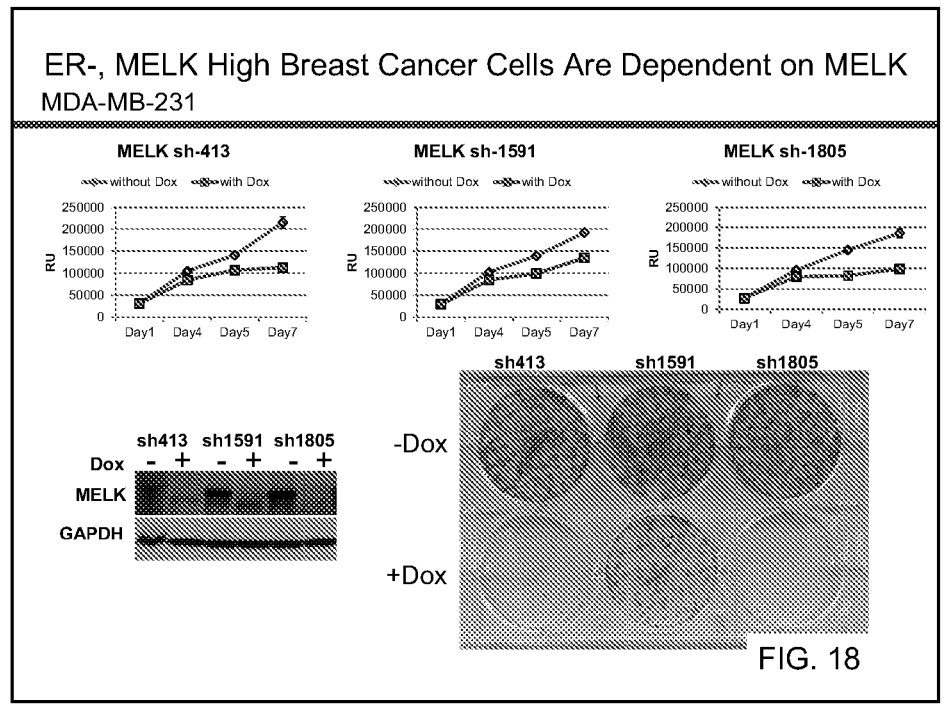

FIG. 18 shows MDA-MB-231 (ER−, MELK high) breast cancer cells are dependent on MELK.

Figure 19:
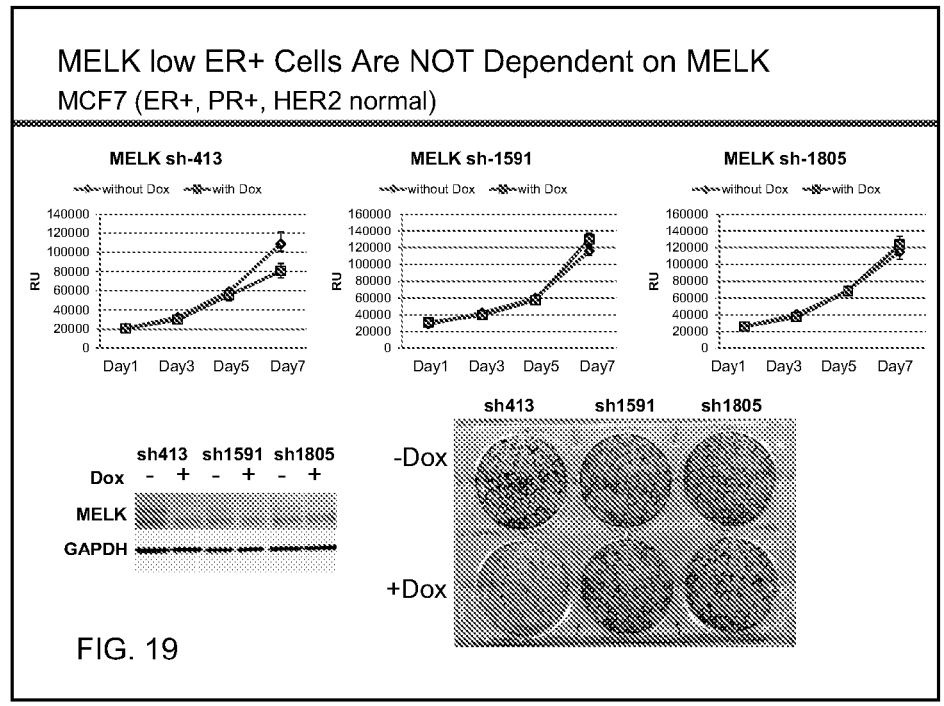

FIG. 19 shows MCF7(ER+, MELK low) breast cancer cells are not dependent on MELK.

Figure 20:
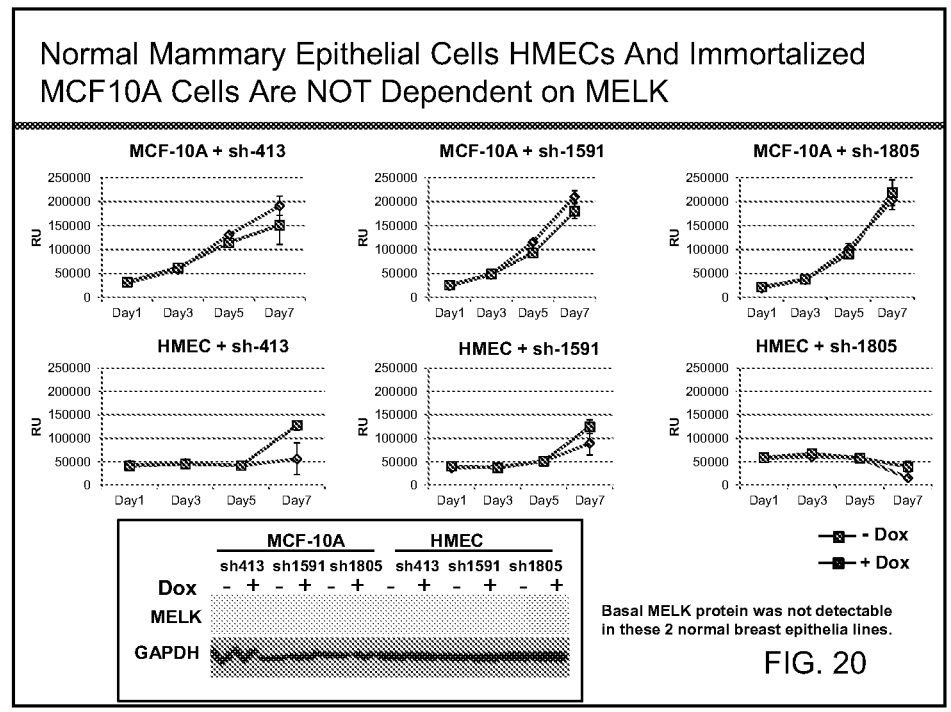

FIG. 20 shows normal mammary epithelial cells (HMEC) and immortalized MCF10A cells are not dependent on MELK.

Figure 21:
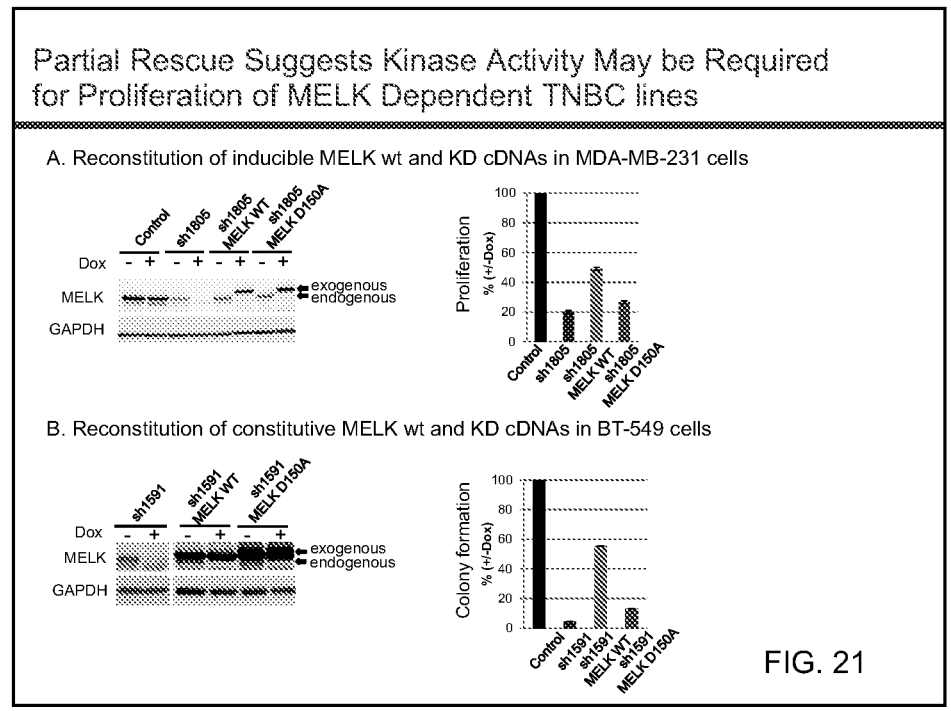

FIG. 21 illustrates that partial rescue suggests kinase activity may be required for proliferation of MELK dependent TNBC lines.

DETAILED DESCRIPTION

The current invention relates to the discovery that Maternal Embryonic Leucine Zipper Kinase (MELK) has been identified as an oncogenic kinase that is essential in ER negative, in basal-like (ER/PR negative), and in triple negative breast cancer cells but not in luminal breast cancer cells, for sustained tumorigenic potential. In addition, MELK has been identified as being critical for the mitotic progression of cells, and is directly regulated by the FoxM1 transcription factor. The current invention also relates to methods of inhibiting growth or proliferation of breast cancer cells and to methods for treating subjects having breast cancer. The current invention further relates to methods of identifying subjects having breast cancer who are likely to benefit from treatment with a MELK inhibitor or a Fox M1 inhibitor.

MELK

Maternal embryonic leucine zipper kinase (MELK) is an atypical member of AMP-activated protein kinase (AMPK) serine/threonine kinase family. MELK has been implicated in stem cell renewal, cell cycle progression, and pre-mRNA splicing. (GeneID 9833.)

FoxM1

The mammalian Forkhead box (Fox) family of transcription factors includes more than 50 mammalian proteins that share homology in the winged helix DNA binding domain. Expression of the FoxM1 transcription factor is induced during the G1 phase of the cell cycle, and its expression continues during S-phase and mitosis). FoxM1 is expressed in all proliferating mammalian cells and tumor-derived cell lines, and its expression is extinguished in terminally differentiated cells that exit the cell cycle. Transcriptional activity of the FoxM1 protein is dependent on Ras-MAPK signaling (Wang et al. 2005). FoxM1 regulates expression of many G2-specific genes and is essential for chromosome stability. Loss of FoxM1 leads to pleiotropic cell-cycle defects, including a delay in G2, chromosome mis-segregation and frequent failure of cytokinesis. Transcriptional activation of cyclin B by FoxM1 is essential for timely mitotic entry (Laoukili et al. 2005).

Breast Cancer

Breast cancer is a heterogeneous disease with a high degree of diversity in histology, therapeutic response, and patient outcomes. Transcriptional profiling analyses have reproducibly identified at least five major "intrinsic" subtypes of breast cancer: normal breast-like, luminal A, luminal B, HER2/Neu-enriched, and basal-like breast cancer (BBC) (Perou et al., 2000; Sorlie et al., 2001). Unlike their luminal counterparts, BBC cells lack expression of estrogen receptor (ER) and progesterone receptor (PR), and thus largely overlap with the clinically defined "triple-negative" breast cancers (TNBC), which is also characterized by the lack of ER/PR expression (Foulkes et al. 2010; Perou 2011). The lack of these molecular targets renders BBC or TNBC cells relatively unresponsive to targeted therapies that are highly effective in the treatment of luminal breast cancer. One aspect of the present invention identifies breast cancer subjects having cancer cells that are estrogen receptor negative ($ER^-$). Another aspect of the present invention identifies breast cancer subjects having cancer cells that are progesterone receptor negative ($PR^-$). Yet another aspect of the present invention identifies breast cancer subjects having cancer cells that are HER2 negative ($HER2^-$). In some embodiments, subjects are identified that are $ER^-$ and $PR^-$. In some embodiments, subjects are identified that are $ER^-$, $PR^-$ and $HER2^-$.

Immunohistochemical or immunoblotting methods may be used to determine the ER, PR and HER2 status of the subjects. Other methods may also be used. An exemplary ER antibody that may be used is 1 D5 antibody, an exemplary PR antibody that may be used is Clone Pgr636 and an exemplary HER2 test that may be used is HercepTest™ (DAKO North America, Carpinteria, Calif.).

Inhibitors

As used herein, the term "inhibit", "inhibiting", or "inhibit the growth or proliferation" of the breast cancer cell refers to slowing, interrupting, arresting or stopping the growth of the breast cancer cell, and does not necessarily indicate a total elimination of the breast cancer cell growth. The terms "inhibit" and "inhibiting", or the like, denote quantitative differences between two states, refer to at least statistically significant differences between the two states. For example, "an amount effective to inhibit growth of breast cancer cells" means that the rate of growth of the cells will be at least statistically significantly different from the untreated cells. Such terms are applied herein to, for example, rates of cell proliferation.

The term "MELK inhibitor" or "FoxM1 inhibitor" refers to any compound capable of inhibiting the expression or activity MELK or FoxM1 respectively, that is to say, in particular, any compound inhibiting the transcription of the gene, the maturation of RNA, the translation of mRNA, the posttranslational modification of the protein, the enzymatic activity of the protein, the interaction of same with a substrate, etc.

Non-limiting examples of inhibitors include RNAi, ribozymes, antisense molecules, aptamers, antibodies, or any type of agonist. In some embodiments, RNA interference may be used to inhibit the expression or activity of MELK or FoxM1 or both MELK and FoxM1. Molecules capable of mediating RNA interference include, but are not limited to, short interfering RNA (siRNA), double-stranded RNA (dsRNA), micro-RNA (miRNA) and short hairpin RNA (shRNA). As used herein, molecules capable of mediating RNAi need not be limited to those molecules containing only RNA, but further encompasses chemically-modified nucleotides and non-nucleotides, referred to as "siNA" molecules "short interfering nucleic acid". Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can include ribonucleotides at about 5, 10, 20, 30, 40, or 50% of the nucleotide positions.

The term "RNA interference (RNAi)" refers to the process of sequence-specific, posttranscriptional gene silencing initiated by molecules capable of mediating RNAI described above (Fire et al., 1998, *Nature*, 391, 806-11). Long double stranded RNA (dsRNA) in cells stimulates the activity of a ribonuclease III enzyme referred to as dicer. Dicer is involved in the processing of the long dsRNA into short pieces of siRNA (Bernstein et al., 2001, *Nature*, 409, 363-6). siRNAs derived from dicer activity are typically about 21-23 nucleotides in length and include duplexes of about 19 base pairs.

The RNAi response also features an endonuclease complex containing a siRNA, commonly referred to as an RNA-induced silencing complex (RISC), which mediates cleavage of single stranded RNA having sequence complementary to the antisense strand of the siRNA duplex. Cleavage of the target RNA takes place in the middle of the region complementary to the antisense strand of the siRNA duplex (Elbashir et al., 2001, *Nature*, 411, 494-498). siRNA mediated RNAi has been studied in a variety of systems. Recent work in *Drosophila* embryonic lysates has revealed certain requirements for siRNA length, structure, chemical composition, and sequence that are essential to mediate efficient RNAi activity (Elbashir et al., 2001, *EMBO J.*, 20, 6877-88). During RNAi, degradation of target mRNA is induced with consequent sequence-specific inhibition of gene expression. The term "small interfering" or "short interfering RNA" or "siRNA" refers to a nucleic acid that forms a double stranded RNA, which double stranded RNA has the ability to reduce or inhibit expression of a gene or target gene when the siRNA is expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. siRNA is "targeted" to a gene in that the nucleotide sequence of the duplex portion of the siRNA is substantially complementary to a nucleotide sequence of the targeted gene. The siRNA sequence duplex needs to be of sufficient length to bring the siRNA and target RNA together through complementary base-pairing interactions. The siRNA of the invention may be of varying lengths. The length of the siRNA is preferably greater than or equal to ten nucleotides and of sufficient length to stably interact with the target RNA; specifically 10-30 nucleotides; more specifically any integer between 10 and 30 nucleotides, such as 10, 11, 12, 13, 14, 15, 16, 17, 18, 19, 20, 21, 22, 23, 24, 25, 26, 27, 28, 29, and 30. By "sufficient length" is meant a nucleotide of greater than or equal to 10 nucleotides that is of a length great enough to provide the intended function under the expected condition. The term "stably interact" refers to interaction of the small interfering RNA with target nucleic acid (e.g., by forming hydrogen bonds with complementary nucleotides in the target under physiological conditions).

The siRNA may be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal. The RNA duplex of the siRNA may be constructed in vitro using synthetic oligonucleotides.

In some embodiments, the inhibitor may be a short hairpin RNA (shRNA) sequence. The term "short hairpin RNA" or "shRNA" refers to RNA molecules having an RNA sequence that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. The sequence of the siRNA can correspond to the full length target gene, or a subsequence thereof. siRNA is "targeted" to a gene in that the nucleotide sequence of the duplex portion of the siRNA is substantially complementary to a nucleotide sequence of the targeted gene as described above. The shRNA may be cloned into a vector using recombinant DNA techniques.

siRNAs may be constructed in vitro using synthetic oligonucleotides or appropriate transcription enzymes or in vivo using appropriate transcription enzymes or expression vectors. The siRNAs include a sense RNA strand and a complementary antisense RNA strand annealed together by standard Watson-Crick base-pairing interactions to form the base pairs. The sense and antisense strands of the present siRNA may be complementary single stranded RNA molecules to form a double stranded (ds) siRNA or a DNA polynucleotide encoding two complementary portions that may include a hairpin structure linking the complementary base pairs to form the siRNA. Preferably, the duplex regions of the siRNA formed by the ds RNA or by the DNA polypeptide include about 15-30 base pairs, more preferably, about 19-25 base pairs. The siRNA duplex region length may be any positive integer between 15 and 30 nucleotides.

The siRNA of the invention derived from ds RNA may include partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion.

One or both strands of the siRNA of the invention may include a 3' overhang. As used herein, a "3' overhang" refers to at least one unpaired nucleotide extending from the 3'-end of an RNA strand. Thus in an embodiment, the siRNA may include at least one 3' overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length.

Both strands of the siRNA molecule may include a 3' overhang, the length of the overhangs can be the same or different for each strand. Preferably, the 3' overhang may be present on both strands of the siRNA, and is 2 nucleotides in length. The 3' overhangs may also be stabilized against degradation. For example, the overhangs may be stabilized by including purine nucleotides, such as adenosine or guanosine nucleotides, by substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2' hydroxyl in the 2'-deoxythymidine significantly enhances the nuclease resistance of the 3' overhang in tissue culture medium.

As described above, the RNA duplex portion of the siRNA may be part of a hairpin structure. The hairpin structure may further contain a loop portion positioned between the two sequences that form the duplex. The loop can vary in length. In some embodiments, the loop may be 5, 6, 7, 8, 9, 10, 11, 12 or 13 nucleotides in length. The hairpin structure may also contain 3' or 5' overhang portions. In some embodiments, the overhang is a 3' or a 5' overhang 0, 1, 2, 3, 4 or 5 nucleotides in length.

The siRNA of the invention may be obtained using a number of techniques known to those of skill in the art. For example, the siRNA may be chemically synthesized using appropriately protected ribonucleoside phosphoramidites and a conventional DNA/RNA synthesizer. The siRNA may be synthesized as two separate, complementary RNA molecules, or as a single RNA molecule with two complementary regions. Commercial suppliers of synthetic RNA molecules or synthesis reagents include Dharmacon Research (Lafayette, Colo., USA), Pierce Chemical (Rockford, Ill., USA), Glen Research (Sterling, Va., USA), ChemGenes (Ashland, Mass., USA) and Cruachem (Glasgow, UK).

Delivery Systems

In some embodiments, the MELK inhibitor and/or the FoxM1 inhibitor may be delivered to the cell using a nucleic acid delivery system, such as a vector. The term "vector" refers to any genetic element, such as a plasmid, phage, transposon, cosmid, chromosome, virus, virion, etc., which is capable of replication when associated with the proper control elements, such as a helper virus, and which can transfer gene sequences between cells. Thus, the term includes cloning and expression vehicles, as well as replication-defective viral vectors. Numerous types of vectors exist and are well known in the art.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "operatively linked" means that a selected nucleic acid sequence, e.g., encoding a siRNA construct is in proximity with a promoter to allow the promoter to regulate expression of the selected nucleic acid sequence. In general, the promoter is located upstream of the selected nucleic acid sequence in terms of the direction of transcription and translation.

The term "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least about 40%, 50%, 60%, 70%, 80%, 90%, 95%, 96%, 97%, 98%, to 99% A sequence identity to the native (endogenous) nucleotide sequence.

The term "conservatively modified variations" of a particular nucleic acid sequence refers to those nucleic acid sequences that encode identical or essentially identical amino acid sequences. Because of the degeneracy of the genetic code, a large number of functionally identical nucleic acids encode any given polypeptide. For instance, the codons CGT, CGC, CGA, CGG, AGA and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill in the art will recognize that each codon in a nucleic acid (except ATG, which is ordinarily the only codon for methionine) can be modified to yield a functionally identical molecule by standard techniques. Accordingly, each "silent variation" of a nucleic acid that encodes a polypeptide is implicit in each described sequence.

The terms "substantially identical" or "substantial identity," in the context of two or more nucleic acids or polypeptide sequences, refer to two or more sequences or subsequences that are the same or have a specified percentage of amino acid residues or nucleotides that are the same (i.e., at least about 60%, preferably 65%, 70%, 75%, preferably 80%, 85%, 90%, 91%, 92%, 93%, 94%, 95%, 96%, 97%, 98% or 99% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence, such as an RNA nucleotide complementary to a DNA nucleotide. Preferably, the substantial identity exists over a region that is at least about 6-7 amino acids or 25 nucleotides in length.

An example of an algorithm that is suitable for determining percent sequence identity and sequence similarity is the BLAST algorithm, which is described in Altschul et al., 1977, Nuc. Acids Res. 25:3389-3402. BLAST is used, with the parameters described herein, to determine percent sequence identity for the nucleic acids and proteins of the invention. Software for performing BLAST analysis is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA, 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA, 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a preselected DNA or RNA duplex into a host cell include, but are not limited to, calcium phosphate precipitation, lipofection, DEAE-dextran, particle bombardment, microinjection, electroporation, immunoliposomes, lipids, cationic lipids, phospholipids, or liposomes and the like. One skilled in the art will understand that any method may be used to deliver the DNA or RNA duplex into the cell.

siRNA Vectors

The siRNA of the present invention may also be expressed from a recombinant plasmid either as two separate, complementary RNA molecules, or as a single RNA molecule with two complementary regions.

Selection of vectors suitable for expressing siRNA of the invention, methods for inserting nucleic acid sequences for expressing the siRNA into the plasmid, and methods of delivering the recombinant plasmid to the cells of interest are within the skill in the art. Methods for constructing recombinant DNA vectors and the production of DNA may be found in Sambrook et al., for example.

The siRNA of the present invention may be a polynucleotide sequence cloned into a plasmid vector and expressed using any suitable promoter. Suitable promoters for expressing siRNA of the invention from a plasmid include, but are not limited to, the H1 and U6 RNA pol III promoter sequences and viral promoters including the viral LTR, adenovirus, SV40, and CMV promoters. Additional promoters known to one of skill in the art may also be used, including tissue specific, inducible or regulatable promoters for expression of the siRNA in a particular tissue or in a particular intracellular environment. The vector may also include additional regulatory or structural elements, including, but not limited to introns, enhancers, and polyadenylation sequences. These elements may be included in the DNA as desired to obtain optimal performance of the siRNA in the cell and may or may not be necessary for the function of the DNA. Optionally, a selectable marker gene or a reporter gene may be included either with the siRNA encoding polynucleotide or as a separate plasmid for delivery to the target cells. Additional elements known to one of skill in the art may also be included.

The siRNA may also be expressed from a polynucleotide sequence cloned into a viral vector that may include the elements described above. Suitable viral vectors for gene delivery to a cell include, but are not limited to, replication-deficient viruses that are capable of directing synthesis of all virion proteins, but are incapable of making infections particles. Exemplary viruses include, but are not limited to lentiviruses, adenoviruses, adeno-associated viruses, retroviruses, and alphaviruses.

In some embodiments, practice of the present invention will employ, unless otherwise indicated, conventional techniques of molecular biology, immunology, microbiology, cell biology and recombinant DNA, which are within the skill of the art. See e.g., Sambrook, Fritsch and Maniatis, MOLECULAR CLONING: A LABORATORY MANUAL, (Current Edition); CURRENT PROTOCOLS IN MOLECULAR BIOLOGY (F. M. Ausubel et al. eds., (Current Edition)); the series METHODS IN ENZYMOLOGY (Academic Press, Inc.): PCR 2: A PRACTICAL APPROACH (Current Edition) ANTIBODIES, A LABORATORY MANUAL and ANIMAL CELL CULTURE (R. I. Freshney, ed. (Current Edition)). DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); Fundamental Virology, 2nd Edition, vol. I & II (B. N. Fields and D. M. Knipe, eds.)

Diagnostic/Prognostic Markers

In some aspects, the present invention relates to methods of detecting the presence of one or more diagnostic or prognostic markers in a sample (e.g. a biological sample from a cancer patient). A variety of screening methods known to one of skill in the art may be used to detect the presence of the marker in the sample including DNA, RNA and protein detection. The techniques described below can be used to determine the presence or absence or amount of MELK and/or FoxM1 in a sample obtained from a patient relative to a sample obtained from a non-cancer subject. In some embodiments, the patient may be tested for ER, PR and/or HER2 receptor status. Identification of MELK and/or FoxM1 or expression levels of MELK and/or FoxM1 in a patient having a $ER^-$, $ER^-/PR^-$ or $ER^-/PR^-/HER2^-$ status assists the physician in determining a treatment protocol for the patient.

In some embodiments, the marker may be an increase in the gene copy number, an increase in protein expression, a change in mRNA expression and the like, for the MELK and/or FoxM1 relative to a control.

By way of non-limiting example, in a patient having an $ER^-$, $ER^-/PR^-$ or $ER^-/PR^-/HER2^-$ status, may indicate the need to treat the patient with a MELK inhibitor, a FoxM1 inhibitor or both a MELK inhibitor and a FoxM1 inhibitor. In some embodiments, patients having increased expression of MELK, Fox M1 or both MELK and FoxM1, may indicate the need to treat the patient with a MELK inhibitor, a FoxM1 inhibitor or both a MELK inhibitor and a FoxM1 inhibitor.

Methods of Treatment

In various embodiments, the invention provides methods for treatment of a patient having cancer. The methods generally comprise administration of an inhibitor. One inhibitor may be a MELK inhibitor. One inhibitor may be a FoxM1 inhibitor. The method may include administration of a MELK inhibitor and a FoxM1 inhibitor.

"Treating", "treat", or "treatment" within the context of the instant invention, means an alleviation of symptoms associated with a disorder or disease, or halt of further progression or worsening of those symptoms, or prevention or prophylaxis of the disease or disorder. For example, within the context of this invention, successful treatment may include an alleviation of symptoms related to breast cancer or a halting in the progression of a disease such as breast cancer.

In some embodiments, the inhibitor is a chemical compound, natural or synthetic, in particular an organic or inorganic molecule of plant, bacterial, viral, animal, eukaryotic, synthetic or semisynthetic origin, capable of inhibiting MELK or FoxM1. A non-limiting examples of a chemical compound that inhibits FoxM1 includes thiostrepton.

As used herein, the term "pharmaceutically acceptable salts" include those salts formed, for example, as acid addition salts, preferably with organic or inorganic acids, from compounds with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, malonic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 4-toluenesulfonic acid, 2-naphthalenesulfonic acid, 1,5-naphthalene-disulfonic acid, 2- or 3-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

The compounds may be used alone or in compositions together with a pharmaceutically acceptable carrier or excipient. Pharmaceutical compositions of the present invention comprise a therapeutically effective amount of a compound formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Other suitable pharmaceutically acceptable excipients are described in "Remington's Pharmaceutical Sciences," Mack Pub. Co., New Jersey, 1991, incorporated herein by reference.

The compounds may be administered to humans and other animals orally, parenterally, sublingually, by aerosolization or inhalation spray, rectally, intracisternally, intravaginally, intraperitoneally, bucally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Methods of formulation are well known in the art and are disclosed, for example, in Remington: *The Science and Practice of Pharmacy*, Mack Publishing Company, Easton, Pa., 19th Edition (1995). Pharmaceutical compositions for use in the present invention can be in the form of sterile, non-pyrogenic liquid solutions or suspensions, coated capsules, suppositories, lyophilized powders, transdermal patches or other forms known in the art.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-propanediol or 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions, which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles.

Aerosolized formulations of the invention may be delivered using an aerosol forming device, such as a jet, vibrating porous plate or ultrasonic nebulizer, preferably selected to allow the formation of an aerosol particles having with a mass medium average diameter predominantly between 1 to 5 μm. Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1-5 μm. Predominantly in this application means that at least 70% but preferably more than 90% of all generated aerosol particles are within 1-5 μm range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AERONEB and AERODOSE vibrating porous plate nebulizers (AeroGen, Inc., Sunnyvale, Calif.), SIDE-STREAM nebulizers (Medic-Aid Ltd., West Sussex, England), PARI LC and PARI LC STAR jet nebulizers (Pari Respiratory Equipment, Inc., Richmond, Va.), and AEROSONIC (DeVilbiss Medizinische Produkte (Deutschland) GmbH, Heiden, Germany) and ULTRAAIRE (Omron Healthcare, Inc., Vernon Hills, Ill.) ultrasonic nebulizers.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

A compound can be administered alone or in combination with another inhibitor, possible combination therapy taking the form of fixed combinations or the administration of a compound and another inhibitor being staggered or given independently of one another. Long-term therapy is equally possible as is adjuvant therapy in the context of other treatment strategies, as described above. Other possible treatments are therapy to maintain the patient's status after tumor regression, or even chemopreventive therapy, for example in patients at risk.

Effective amounts of the compounds of the invention generally include any amount sufficient to detectably inhibit the growth or proliferation of breast cancer cells, or by detecting an inhibition or alleviation of symptoms of breast cancer. The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

According to the methods of treatment of the present invention, breast cancer cell growth is reduced or prevented in a patient such as a human or lower mammal by administering to the patient an amount of an inhibitor, in such amounts and for such time as is necessary to achieve the desired result. An "amount that is effective to inhibit growth or proliferation of the breast cancer cells" of a compound of an inhibitor refers to a sufficient amount of the inhibitor to treat breast cancer cell growth, at a reasonable benefit/risk ratio applicable to any medical treatment.

It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The dose of the MELK inhibitor or the FoxM1 inhibitor to be administered alone or in combination therapy warm-blooded animals, for example humans, is preferably from approximately 0.01 mg/kg to approximately 1000 mg/kg, more preferably from approximately 1 mg/kg to approximately 100 mg/kg, per day, divided preferably into 1 to 3 single doses which may, for example, be of the same size. Usually children receive half of the adult dose, and thus the preferential dose range for the inhibitor in children is 0.5 mg/kg to approximately 500 mg/kg, per day, divided preferably into 1 to 3 single doses that may be of the same size.

The general terms used hereinbefore and hereinafter preferably have within the context of this disclosure the following meanings, unless otherwise indicated.

The following Examples serve to illustrate the invention without limiting the invention in its scope.

EXAMPLE 1

Figure 1:
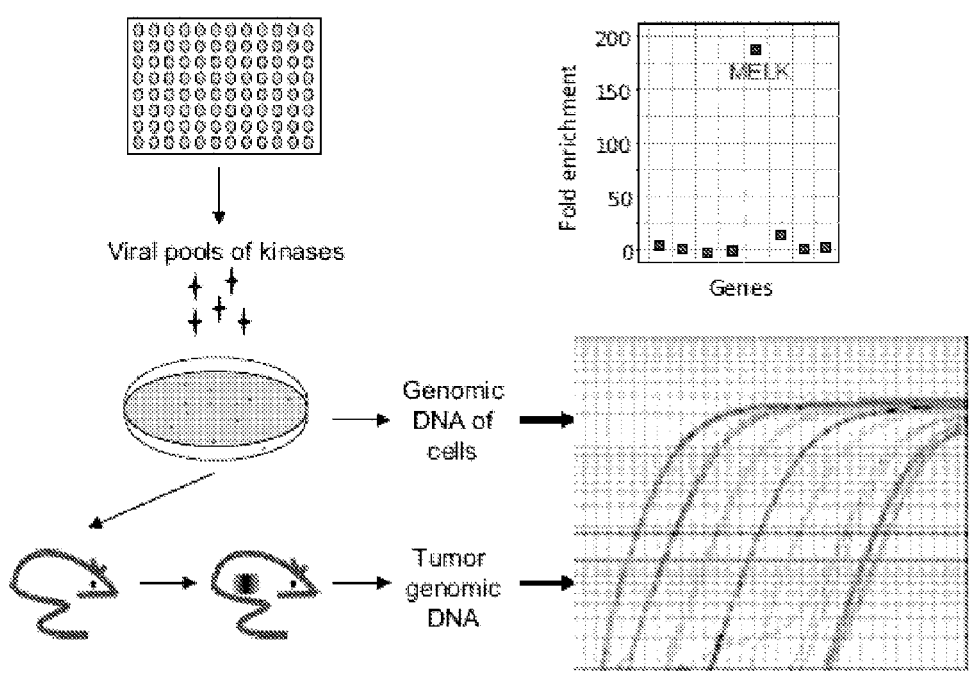
FIG. 1 illustrates an in vivo genetic screen that identifies MELK as a potential oncogene.

Identification of Oncogeinc Kinases that Contribute to Tumorigenesis of HMECs In Vivo Transformation of primary human cells with defined genetic elements is a powerful method for identifying specific genes or pathways that are involved in oncogenic transformation (Hahn et al., 1999; Zhao et al., 2004). To this end, an in vivo tumorigenesis model was developed that resembles the pathogenesis of human breast cancer. A human mammary epithelial cell (HMEC) based transformation system suitable for the study of oncogenic kinases was previously established (Zhao et al., 2003). To further optimize this system, HMECs were engineered to express a dominant negative form of p53 (p53DD), NeuT and PI3KCA H1047R. The resulting cells, termed HMECs-DD-NeuT-PI3KCA, were fully transformed as judged by their ability to form orthotopic tumors in mice (FIG. 1A). This model resembles the concurrent activation of ErbB2 and PI3KCA that is prevalent in breast cancer (Stephens et al., 2012).

Next, a retrovirus-based kinase library (Boehm et al., 2007) was utilized and a screen for kinases that can replace oncogenic PIK3CA and cooperate with NeuT to drive tumorigenesis in mice was conducted. HMEC-DD-NeuT cells were infected with subpools of a kinome-wide retroviral library encoding 354 myristoylated human kinases and kinase-related proteins (Boehm 2007). 37 subpools of 10-12 unique kinase ORFs were introduced into HMECs-DD-NeuT cells. The infected cells were then injected into the inguinal mammary fat pads of nude mice, and recipient mice were followed for tumor formation. Kinases in 12 out of 37 pools induced tumor formation with latencies of 2-4 months. Genomic DNA was extracted from harvested tumor specimens and infected cells prior to injection. Quantitative PCR was used to determine the relative abundance of each kinase in the candidate pool in the tumors. In total, twenty-six kinases were found that were specifically enriched during the development of tumors (FIG. 2A, 2B). Several kinases that emerged as hits have previously been implicated as proto-oncogenes or cancer-associated genes, such as inhibitor of nuclear factor kappa-B kinase subunit epsilon (IK-BKE) (Boehm 2007), rearranged during transfection (RET) (Takahashi, 1985), casein kinase 1 epsilon (CSNK1E) (Kim 2010), NIMA-related serine/threonine kinase 6 (NEK6) (Nassirpour et al., 2010), and polo-like kinase 1 (Plk1) (Liu et al., 2006).

EXAMPLE 2

MELK is Highly Overexpressed in Breast Cancer and Strongly Predicts Poor Outcomes One of the top-scoring hits from the genetic screen described in Example 1 was the maternal embryonic leucine zipper kinase (MELK) (FIG. 2A), an atypical member of AMPK serine/threonine kinase family (Lizcano et al., 2004). While little is known about the exact biological functions of MELK, this kinase is frequently overexpressed in a variety of tumors (Gray et al., 2005). Remarkably, when we analyzed MELK expression in the breast cancer dataset of The Cancer Genome Atlas (TCGA) (Koboldt et al., 2012), a large cohort consisting of 392 invasive ductal breast carcinomas and 61 samples of normal breasts, the level of MELK transcript was approximately 8-fold higher in breast cancers compared to their normal counterparts (FIG. 2A). The p value for this differential expression ($4.6 \times 10^{-54}$) places MELK as a top 1% overexpressed gene in breast cancer (FIG. 2A). The overexpression of MELK in breast carcinoma relative to normal breasts was further confirmed by analyzing two other independent datasets (FIG. 4A; Richardson et al., 2006; Ma et al., 2009).

To gain insights into the potential relevance of MELK overexpression to breast cancer, MELK expression was analyzed for correlation with the status of disease. By analyzing gene expression data across five independent, large cohorts totaling more than 1500 patients (Desmedt et al., 2007; Hatzis et al., 2011; Schmidt et al., 2008; Wang et al., 2005; Table S1), higher expression of MELK was found to be strongly associated with greater histologic grade of breast cancer (FIG. 2B, 4B); the p values for this correlation all rank top 1% among the total 12,624 or more genes measured. See also FIGS. 14, 15)

MELK expression was also examined to determine whether expression of MELK is correlated with metastatic recurrence. Three independent cohorts in which patients with early-stage breast cancer were followed for metastasis-free survival and had not received adjuvant systemic treatment after surgery were analyzed (van't Veer, Wang, and Schmidt cohorts; Table S1). In all the three cohorts, high MELK expression was strongly associated with earlier metastasis in women initially diagnosed with lymph-node-negative tumors (all p values <0.001, hazard ratios >2; FIG. 3C, 4C). Two cohorts were further analyzed where a majority of patients had high grade and lymph-node-positive breast cancer and nearly all patients received neoadjuvant chemotherapy and/or hormone therapy (Hatzis, Loi cohorts; Table S1 below). Again, high expression of MELK robustly predicted metastasis recurrence (both p values <0.001, hazard ratios >2; FIG. 2C). Thus, MELK overexpression is a strong predictive marker for breast cancer metastasis irrespective of chemotherapy or hormone therapy. The analysis also indicates that breast cancer with high expression of MELK is associated with high malignancy and is less responsive to conventional breast cancer therapies.

MELK expression was analyzed for predictive value in the survival of breast cancer patients. In five independent large cohorts where more than 1100 total patients were followed for overall survival (Desmedt et al., 2007; Esserman et al., 2012; Kao et al., 2011; Pawitan et al., 2005; van de Vijver et al., 2002; Table S1), high expression of MELK strongly correlated with increased rate of mortality (all p values <0.05, hazard ratios >2) (FIG. 2D, 4D). Together, these data implicate MELK as a robust prognostic indicator, which identifies breast cancer patients with higher histological grade of disease, increased likelihood of metastasis and lower overall survival rates.

TABLE S1

Breast Cancer Gene Expression Datasets used in this Study
(supplement for FIGS. 2, 4, 7C, 137C)

| | n | References |
|---|---|---|
| For comparing MELK expression in | Normal breast vs carcinoma | |
| TCGA_breast | 61 vs 392 | Koboldt et al., (2012) Nature |
| Richardson_breast | 7 vs 40 | Richardson et al., (2006) Cancer Cell |

TABLE S1-continued

Breast Cancer Gene Expression Datasets used in this Study
(supplement for FIGS. 2, 4, 7C, 137C)

| | n | References |
|---|---|---|
| Ma_breast | 14 vs 18 | Ma et al., (2009) Breast Cancer Res |
| For analysis of disease grade | | |
| Desmedt_breast | 198 | Desmedt et al., (2007) Clin Cancer Res |
| Schmidt_breast | 200 | Schmidt et al., (2008) Cancer Res |
| Bittner_breast | 336 | unpublished |
| Hatzis_breast | 508 | Hatzis et al., (2011) JAMA |
| Wang_breast | 286 | Wang et al., (2005) Lancet |
| For analysis of metastasis-free survival | | |
| Schmidt_breast | 200 | Schmidt et al., (2008) Cancer Res |
| Loi_breast | 87 | Loi et al, (2007) J Clin Oncol |
| van't_Veer_breast | 117 | van't Veer et al., (2002) Nature |
| Wang_breast | 286 | Wang et al., (2005) Lancet |
| Hatzis_breast | 508 | Hatzis et al., (2011) JAMA |
| For analysis of overall survival | | |
| van de Vijver_breast | 295 | van de Vijver et al., (2002) N Engl J Med |
| Desmedt_breast | 198 | Desmedt et al., (2007) Clin Cancer Res |
| Esserman_breast | 130 | Esserman et al., (2012) Breast Cancer Res Treat |
| Pawitan_breast | 159 | Pawitan et al., (2005) Breast Cancer Res |
| Kao_breast | 327 | Kao et al., (2011) BMC Cancer |
| For correlative analysis of gene expression | | |
| TCGA_breast | 392 | Koboldt et al., (2012) Nature |
| Bittner_breast | 261 | unpublished |
| van de Vijver_breast | 295 | van de Vijver et al., (2002) N Engl J Med |
| Hatzis_breast | 508 | Hatzis et al., (2011) JAMA |

EXAMPLE 3

Ovexpression of MELK in Different Subtypes of Breast Cancer

Given the heterogeneity of breast cancer, MELK expression was analyzed in different subtypes of breast cancer as defined by gene expression profiling (Perou et al., 2000; Sorlie et al., 2001). Samples in multiple breast cancer datasets were characterized by PAM50 gene signature (Parker et al., 2009). In four independent cohorts totaling more than 1200 patients, a strikingly similar pattern of MELK expression was observed among these different subtypes (FIG. 3E, 4E). Luminal A and normal-like subtypes displayed the lowest expression of MELK. Luminal B tumors, which have lower expression of luminal-specific genes (Solie et al., 2001) and HER2-enriched tumors had higher MELK expression than luminal A or normal-like tumors (p<0.0001). Finally, basal-like breast cancers (BBC) showed the highest expression of MELK among all subtypes (p<0.0001). These observations indicate a pattern that MELK expression negatively correlates with the expression of luminal makers. Indeed, a significant inverse correlation between the expression of MELK and estrogen receptor (ER or ESR1) was found (FIG. 3F, 4F, 14A).

An alternate categorization of breast cancers uses the expression of ER/PR and HER2. Triple-negative breast cancer (TNBC), a subtype lacking ER/PR and HER2 expression, largely overlaps with basal-like breast cancer (Foulkes et al., 2010; Rakha et al, 2008.). Because subtype-categorization as TNBC has been routinely used in the clinic for diagnosis and selection of treatment strategies, correlation of MELK expression with this alternate subtype categorization was examined. In two independent cohorts (Table S1), samples were grouped into subtypes based on expression of ER/PR and HER2. Indeed, the expression level of MELK is the highest in TNBC, medium in HER2+, and lowest in ER/PR+ breast cancers (FIG. 4G). Together, these data indicate that MELK is differentially overexpressed in TNBC or BBC.

EXAMPLE 4

MELK Overexpression Displays Robust Oncogenic Activity

The significant prognostic value of MELK together with its marked overexpression in (especially basal-like) breast cancer, suggested that MELK might play a crucial role in oncogenesis. Since only a few mutations in MELK have been identified in human cancers, overexpression of wild-type MELK was hypothesized to be sufficient for oncogenesis. First, confirmation that overexpression of MELK can promote tumor formation in HMEC-DD-NeuT cells, the model system used in the initial tumorigenesis screen, was tested. HMEC-DD-NeuT cells were re-engineered to express wildtype (wt-) or myristoylated (myr-) MELK (note: the kinases in the initial screen were myristoylated (Boehm et al., 2007)). While HMEC-DD-NeuT cells expressing the empty vector failed to form tumors in mice, overexpression of WT- or myr-MELK in these cells rendered tumor formation with 100% penetrance within two months (FIG. 5A).

To determine whether MELK has a "stand-alone" transforming capacity that is independent of ErbB2, a rodent fibroblast (Rat1) transformation system was used in which a single oncogene is sufficient to achieve malignancy transformation of Rat1 cells expressing p53DD (Rat1-DD) (Zhao et al., 2004). It was recently demonstrated that expression of an oncogenic PI3KCA H1047R in the absence of NeuT, was sufficient to induce tumor formation in Rat1-DD (Ni et al., 2012). We engineered Rat1-DD cells expressing MELK (Rat1-DD-MELK), or PI3KCA H1047R (Rat1-DD-PI3KCA H1047R) as a positive control (FIG. 3B). Rat1-DD cells expressing an empty vector failed to grow as colonies in soft agar or to form tumors in mice. Strikingly, Rat1-DD-MELK cells displayed a comparably robust transforming activity to Rat1-DD-PI3KCA H1047R cell, as evidenced by both colony growth in vitro and tumor formation in vivo (FIG. 2C, 2D).

Finally, to determine whether the kinase activity of MELK is essential for its transforming potential, catalytically inactive forms of MELK, D150A or T167A (Lizcano et al., 2004; Vulsteke et al., 2004), were introduced into Rat-DD cells. Unlike Rat1-DD-MELK cells, both Rat1-DD-MELK-D150A and Rat1-DD-MELK-T157A cells exhibited only limited growth in soft agar or in mice (FIG. 3E, 3F, 3G). Together, these studies indicate that MELK can be a very potent oncogenic driver when it is aberrantly overexpressed and that this oncogenic potential relies on the kinase activity of MELK.

EXAMPLE 5

MELK is Critical for the Oncogenic Potential of BBC Cells Both In Vitro and In Vivo The oncogenic potential of MELK led to the hypothesis that MELK might be essential for the proliferation of BBC, the subtype of breast cancer where MELK was found to expressed at the highest level (FIG. 3E, 14). For these studies, a set of breast cancer cell lines that mirror the molecular subtypes found in clinical tumors (Neve et al., 2006) were used. These cells have been extensively characterized and have previously been used to develop subtype-specific therapies. The cell lines corresponding to BBC displayed high expression level of MELK. (FIG. 15B) In the Neve dataset, all 23 BBC cells showed a significant increase in MELK expression compared to the 24 luminal cells (FIG. 6A). When the cell lines were grouped by expression of hormone receptors (ER/PR) and HER2, all 21 triple-negative breast cancer cell lines expressed MELK at a higher level than ER/PR+ cells (FIG. 7A). These results are consistent with the expression pattern of MELK in human breast cancer (FIG. 3E, 4E, 4F). The protein abundance of MELK is much higher in BBC cells compared to luminal cells (MCF7 and T47D) as confirmed by immunoblotting (FIG. 4B). These cell lines thus provide an excellent platform to assess the cellular functions of MELK.

To examine the role of MELK in the proliferation of these cells, a conditional gene knockdown technique in which shRNA transcription (and consequently target gene silencing) is induced only upon exposure to doxycycline was used (Wiederschain et al., 2009). Among the multiple inducible shRNAs that were generated to target MELK, four MELK target sequences were identified and shRNAs directed to the target sequences were found to efficiently silence MELK expression and inhibit cell growth in cells treated with doxycycline (FIG. 6C, 6D, 7B, 16, 17, 19). The MELK target sequences and the forward and reverse primers for making the shRNAs are shown in Table 1 below.

TABLE 1

| MELK ID | MELK Target Sequence | SEQ. ID. NO. |
|---|---|---|
| MELK sh-413 | GAGAGCTGTTTGACTATATAA | SEQ. ID. NO: 1 |
| MELK-1805 | GACTAAAGCTTCACTATAATG | SEQ. ID. NO: 2 |
| shMELK 1 | GGTGTGATACAGCCTACATAA | SEQ. ID. NO: 3 |
| MELK sh 1591 and shMELK2 | GCCTGAAAGAAACTCCAATTA | SEQ. ID. NO: 4 |

| Oligo | Sequence | |
|---|---|---|
| MELK sh-413 forward | CCGGGAGAGCTGTTTGACTATATAACTCGAGTTATATAGTCAAACAGCTCTCTTTTTG | SEQ. ID. NO: 5 |
| MELK sh-413 reverse | AATTAAAAAGAGAGCTGTTTGACTATATAACTCGAGTTATATAGTCAAACAGCTCTCT | SEQ. ID. NO: 6 |
| MELK-1805 forward | CCGGGACTAAAGCTTCACTATAATGCTCGAGCATTATAGTGAAGCTTTAGTCTTTTTG | SEQ. ID. NO: 7 |

TABLE 1-continued

| | | |
|---|---|---|
| MELK-1805 reverse | AATTAAAAAGACTAAAGCTTC ACTATAATGCTCGAGCATTAT AGTGAAGCTTTAGTCT | SEQ. ID. NO: 8 |
| shMELK1 forward | CCGGGGTGTGATACAGCCTAC ATAACTCGAGTTATGTAGGCT GTATCACACCTTTTTG | SEQ. ID. NO: 9 |
| shMELK1 reverse | AATTCAAAAAGGTGTGATACA GCCTACATAACTCGAGTTATG TAGGCTGTATCACACC | SEQ. ID. NO: 10 |
| MELK sh-1591 and shMELK2 forward | CCGGGCCTGAAAGAAACTCCA ATTACTCGAGTAATTGGAGTT TCTTTCAGGCTTTTG | SEQ. ID. NO: 11 |
| MELK sh-1591 and shMELK2 reverse | AATTCAAAAAGCCTGAAAGAA ACTCCAATTACTCGAGTAATT GGAGTTTCTTTCAGGC | SEQ. ID. NO: 12 | shMELK1, shMELK2, MELK sh-413, MELK sh-1591 and MELK sh-1805 were stably introduced into basal breast cancer cells as well as into two luminal cell lines and cell proliferation was examined upon induction of the shRNA. As shown, induction of MELK knockdown via doxycycline strongly impaired the growth of BBC cells including BT549, MDA-MB-468, MDA-MB-231, and MDA-MB-436 (FIG. 6C, 7A, 16-18); by contrast, the two luminal cell lines, MCF7 and T47D, which have significantly lower expression of MELK (FIG. 6B, 19), were protected from the induction of MELK silencing (FIG. 6D, 19). To confirm that these effects are due to the specific knockdown of MELK, MELK expression was rescued by stably introducing a doxycycline-inducible and shMELK-resistant MELK (MELK-R) (FIG. 6E, left panel; 7B). In MDA-MB-468 cells expressing shMELK, cell proliferation was restored to the normal level when MELK expression was rescued (FIG. 6E, middle and right panels). Interestingly, a shRNA-resistant but kinase inactive version of MELK, MELK-R (T167A), failed to restore cell proliferation (FIG. 6E), indicating that kinase activity of MELK is critical for the proliferation of BBC cells.

The requirement of MELK in BBC cells for their onco-genic growth was also examined. First, in vitro, both control MDA-MB-468 and MDA-MB-231 cells readily grew into macroscopic colonies in soft agar. In contrast, induction of MELK knockdown in these cells by doxycycline caused a nearly complete inhibition in colony formation (FIG. 8A, 17, 18). Next, it was examined whether MELK is essential for the in vivo tumorigenesis of BBC cells. Breast cancer cells with stable shMELK were transplanted into the mammary fat pads of immunocompromised mice to allow orthotopic tumor formation. In mice carrying established tumors, doxycycline-administration induced efficient MELK suppression (FIG. 9), validating the suitability of the inducible shRNA system in vivo. Treating mice with doxycycline immediately following transplantation strongly inhibited the formation of orthotopic tumors (FIG. 8B, 8C), demonstrating that MELK is required for these BBC cells to grow in vivo. To further examine whether MELK is required for the maintenance of established xenograft tumors in vivo, mice bearing xenograft tumors derived from basal-like or luminal breast cancer cells were treated with doxycycline. Remarkably, down-regulation of MELK substantially regressed tumors arising from BBC cells but has little effect on luminal cancer cell-derived tumors (FIG. 8D-G, FIG. 9). Together, these data indicate the MELK is selectively required for the proliferation of BBC cells both in vitro and in vivo.

EXAMPLE 6

Loss of MELK Causes Defective Mitosis and Cell Death in BBC Cells

To understand the mechanisms underlying the role of MELK in BBC cells, MELK depletion was examined for impact in various cellular processes. In cells treated with doxycycline, apoptotic markers, including cleaved caspase 3, cleaved PARP and DNA fragmentation were consistently observed (FIG. 10A, 10B, FIG. 11). zVad, a pan-caspase inhibitor, significantly reduced MELK knockdown-induced cell death, indicating an active role of caspases in executing cell death upon MELK depletion (FIG. 10C, FIG. 11B). Notably, cell death induced by MELK knockdown only occurred in BBC cells but not in luminal tumor cells, such as MCF7 (FIG. 10D, FIG. 11C), providing a plausible explanation for the selective requirement of MELK in basal-like, but not luminal, breast cancer cells.

In parallel, the effect of MELK depletion on cell cycle was investigated. Knocking-down MELK in cells upon doxycycline treatment induced an obvious accumulation of cells with 4n DNA content (FIG. 10E, FIG. 11D, left and middle panels), indicating an induction of G2/M arrest. Consistent with this, cells exposed to doxycycline had elevated markers of mitosis, such as Cyclin B1, Aurora kinase A (FIG. 10E, FIG. 11D, right panels). Interestingly, doxycycline induced a nearly two-fold increase in the percentage of cells with two or more nuclei as shown in the imaged cells (FIG. 10F, FIG. 11E), indicating a failure of cytokinesis. Furthermore, cells with MELK depletion displayed a variety of mitotic aberrations, such as monopolar spindles, mis-localized centrosomes, mis-segregation of sister chromatids, and asymmetric division (FIG. 10G).

The concurrent cell death and defective mitosis upon MELK knockdown was examined for functional association. Using time-lapse microscopy, cells expressing GFP-Histone 2B, a marker for chromosome dynamics in live cells were examined (Kanda et al., 1998). When MELK expression is downregulated, cells with double nuclei rather than neighboring cells with single nucleus underwent cell death (FIG. 10H, middle panel). Another scenario in the presence of doxycycline, cells with an apparent metaphase plate were unable to progress towards anaphase, ending with cell death (FIG. 10H, bottom panel). By contrast, the control cell readily progressed from metaphase to anaphase (FIG. 10H, top panel). Together, these data suggest a model in which BBC cells rely on MELK for proper mitosis; inhibiting MELK in these cells causes impaired mitosis and consequently cell death.

EXAMPLE 7

FoxM1 is Overexpressed in BBC and Regulates MELK Expression

MELK was examined to determine if MILK is a mitotic kinase in BBC cells. MELK was highly accumulated in mitotic cells, which were enriched through nocodazole-induced prometaphase arrest (FIG. 12A, FIG. 13A).

When the arrested cells were released from nocodazole and readily progressed into G1 phase, MELK protein abundance was dramatically decreased (FIG. 12A, FIG. 13A). This expression pattern is typical of those classic mitotic factors, such as Cyclin B1 and Aurora kinases (FIG. 12A, FIG. 13A), suggesting that MELK is a mitotic kinase.

MELK regulation by FoxM1, a master regulator of a variety of genes that are essential for mitosis, was examined (Laoukili et al., 2005; Wang et al., 2005). Interestingly, like MELK, FoxM1 is most highly expressed in the BBC or TNBC subtypes (FIG. 12B, FIG. 13B. 13C). Moreover, an extremely tight correlation between FoxM1 and MELK expression was observed in multiple large-sized cohorts (FIG. 12C, FIG. 13D). Inhibiting FoxM1 via gene silencing using siRNA (SEQ ID NO: 31) or a chemical inhibitor (thiostrepton) reduced the abundance of MELK (FIG. 12D, 12E, FIG. 13E). Furthermore, we found that the promoter of MELK contains a putative FoxM1 binding motif (SEQ ID NO: 45, shown in FIG. 12F) (Wierstra and Alves, 2007) and a chromatin immunoprecipitation assay using antibody against FoxM1 recovered the MELK promoter region with the putative binding site (FIG. 12E, 12F). Together these studies identify FoxM1 as a transcription factor that is enriched in BBC and regulates MELK, providing a molecular mechanism underlying the overexpression of MELK in BBC.

Experimental Procedures

Plasmids

The human MELK was amplified using the template DNA deposited in the describe kinase library, and cloned into pWZL retroviral vector (Zhao et al., 2003), in which target gene expression is driven by the long terminal repeat of Moloney murine leukemia virus. The MELK mutants (D150A, T167A, or shMELK-resistant MELK with silent mutations) were generated via Quickchange XL Site-directed Mutagenesis (Stratagene). Primers are listed in Table S2 below. To construct a tetracycline-inducible gene expression system, GFP or mutated MELK was amplified using the primers listed in Table S2. The PCR products were digested with AgeI and PacI, and ligated with digested pLKO-TREX (Wee et al., 2008).

To construct pWzl-H2B-GFP, human Histone 2B was amplified using the genomic DNA of HEK293T cells as templates. Primers for cloning are listed in Table S2. PCR products following digestion with BamHI and XhoI were ligated with digested pWzl-GFP. To generate pLKO-tet-on-shRNAs targeting human MELK, oligonucleotides were designed and synthesized (IDT). Following annealing, double-stranded oligonucleotides were directly ligated with pLKO vector that was digested with AgeI and EcoRI. The sequences for scramble, shMELK1, shMELK2 are listed in Table S2. Retroviruses were generated by transfecting HEK293T cells with pWzl plasmids and packaging DNA. Typically 1.6 µg pWzl DNA, 1.2 µg pCG-VSVG and 1.2 µg pCG-gap/pol, 12 µl lipid of Metafectene Pro (Biontex) were used; DNA and lipid were diluted in 300 µl PBS respectively and mixed; and following 15 min of incubation, they were added to one 6-cm dish that was seeded with 3 million HEK293T cells one day earlier. Viral supernatant was collected 48 h and 72 h after transfection. After the supernatant was filtered through a 0.45 µm membrane, it was added to target cells in the presence of 8 µg/ml polybrene (Millipore). Lentiviruses were generated with a similar approach with the exception of cells that were transfected with 2 µg pLKO DNA, 1.5 µg pCMV-dR8.91, and 0.5 µg pMD2-VSVG. Cells were selected with antibiotics starting 72 h after initial infection. Puromycin and blasticidin were used at the final concentrations of 1.5 µg/ml and 4 µg/ml respectively.

TABLE S2

| Table S2 Oligonucleotides | | SEQ. ID. NO. |
|---|---|---|
| GFP primers for constructing pLKO-TREX-GFP | | |
| Forward | 5'-gatcaccggtatggtgagcaagggcgagga-3' | SEQ. ID. NO: 13 |
| Reverse | 5'-gatcttaattaattacttgtacagctcgtcca-3' | SEQ. ID. NO: 14 |
| MELK primers for constructing pLKO-TREX-Flag-MELK | | |
| Forward | 5'-gatcaccggtgccaccatggactacaaagacgatgacgacaagaaagattatgatgaacttct-3' | SEQ. ID. NO: 15 |
| Reverse | 5'-gatcttaattaattataccttgcagctagataggat-3' | SEQ. ID. NO: 16 |
| Histon 2B primers for constructing pWzI-H2B-GFP | | |
| Forward | 5'-gatcggatccgccaccatgcctgagccagccaagtc-3' | SEQ. ID. NO: 17 |
| Reverse | 5'-gatcctcgagcttggagctggtgtacttgg-3' | SEQ. ID. NO: 18 |
| Mutagenesis primers for MELK (D150A) | | |
| Forward | 5'-tatcataaattaaagctgattgcctttggtctctgtgcaaaaccc-3' | SEQ. ID. NO: 19 |
| Reverse | 5'-gggttttgcacagagaccaaaggcaatcagctttaatttatgata-3' | SEQ. ID. NO: 20 |
| Mutagenesis primers for MELK (T167A) | | |
| Forward | 5'-aggattaccatcta caggcatgctgtgggagtctg-3' | SEQ. ID. NO: 21 |
| Reverse | 5'-cagactcccacagcatgcctgtagatggtaatcct-3' | SEQ. ID. NO: 22 |
| Mutagenesis primers for shMELK2-resistant MELK | | |
| Forward | 5'-caaaagctagaaaccagtgcctgaaggagacacctattaaaataccagtaaattcaacag-3' | SEQ. ID. NO: 23 |
| Reverse | 5'-ctgttga atttactggtattttaataggtgtctccttcaggcactggtttctagcttttg-3' | SEQ. ID. NO: 24 |

TABLE S2-continued

| Table S2 Oligonucleotides | | SEQ. ID. NO. |
|---|---|---|

Oligo for constructing pLKO-tet-on-scramble

| Forward | 5'-ccgggtggactcttgaaagtactatctcgagatagtactttcaagagtccacttttttg-3' | SEQ. ID. NO: 25 |
| Reverse | 5'-aattaaaaagtggactcttgaaagtactatctcgagatagtactttcaagagtccac-3' | SEQ. ID. NO: 26 |

Oligo for constructing pLKO-tet-on-shMELK1

| Forward | 5'-ccggggtgtgatacagcctacataactcgagttatgtaggctgtatcacaccttttttg-3' | SEQ. ID. NO: 9 |
| Reverse | 5'-aattcaaaaaggtgtgatacagcctacataactcgagttatgtaggctgtatcacacc-3' | SEQ. ID. NO: 10 |

Oligo for constructing pLKO-tet-on-shMELK2

| Forward | 5'-ccgggcctgaaagaaactccaattactcgagtaattggagtttctttcaggcttttttg-3' | SEQ. ID. NO: 11 |
| Reverse | 5'-aattcaaaaagcctgaaagaaactccaattactcgagtaattggagtttctttcaggc-3' | SEQ. ID. NO: 12 |

Oligo for constructing pLKO-tet-on-shFoxM1

| Forward | 5'-ccggggaccactttccctactttaactcgagttaaagtagggaaagtggtccttttttg-3' | SEQ. ID. NO: 27 |
| Reverse | 5'-aattcaaaaaggaccactttccctactttaactcgagttaaagtagggaaagtggtcc-3' | SEQ. ID. NO: 28 |
| siFoxM1 | ggaccacuuucccuacuuu (Fu et al., 2008; Wang et al., 2005) | SEQ. ID. NO: 29 |

Primers used in chromatin immunoprecipitation experiments

| MELK-Fwrd | 5'-aggctgaggcgggaggatcgctt-3' | SEQ. ID. NO: 30 |
| MELK-rv | 5'-gtgttgccacgaggaataagaacc-3' | SEQ. ID. NO: 31 |
| CDC25B-Fwr | 5'-aagagcccatcagttccgcttg-3' | SEQ. ID. NO: 32 |
| CDC25B-Rv | 5'-aagagcccatcagttccgcttg-3' | SEQ. ID. NO: 33 |

Primers used in q-PCR experiments

| MELK-Fwrd | 5'-aaacccaagggtaacaagga-3' | SEQ. ID. NO: 34 |
| MELK-rv | 5'-acagtatgcccatgctccaa-3' | SEQ. ID. NO: 35 |
| CENPA-Fwrd | 5'-cttcctcccatcaacacagtcg-3' | SEQ. ID. NO: 36 |
| CENPA-rv | 5'-tgcttctgctgcctcttgtagg-3' | SEQ. ID. NO: 37 |
| BIRC5-Fwrd | 5'-tcaaggaccaccgcatctcta-3' | SEQ. ID. NO: 38 |
| BIRC5-rv | 5'-tgaagcagaagaaacactgggc-3' | SEQ. ID. NO: 39 |

| MELK and MELK-R target sequences | | |
|---|---|---|
| MELK | TGCCTGAAAGAAACTCCAATTAAA | SEQ. ID. NO: 40 |
| MELK-R | TGCCTGAAGGAGACACCTATTAAA | SEQ. ID. NO: 41 |

| Human MELK promoter | | |
|---|---|---|
| | ACCCACAAATAATTTAG | SEQ. ID. NO: 42 |

| FoxM1 consensus site | | |
|---|---|---|
| | AC/TAAAC/TAANN | SEQ. ID. NO: 43 |

Cell Culture

Human mammary epithelial cells (HMECs) were maintained in DMEM/F-12 supplemented with EGF (10 ng/ml), insulin (10 µg/ml), and hydrocortisone 0.5 µg/ml) under 5% $CO_2$ and 37° C. Rat1 and HEK293T cells were maintained in DMEM supplemented with 10% FBS (Invitrogen). All breast cancer cell lines (MCF7, T47D, MDA-MB-468, MDA-MB-231, MDA-MB-436, HCC1197, BT549) were cultured in RPMI 1640 medium supplemented with 10% FBS. For cells stably introduced with tetracycline-inducible genes/shRNAs, Tet-approved FBS (Clontech) was used.

Cell Proliferation Assay

Typically, breast cancer cells were seeded in 12-well plates ($1-2 \times 10^4$) in 1 ml medium. On the next day, wells were added with 110 µl medium without or with 1 µg/ml doxycycline (to reach a final concentration of 100 ng/ml), which was repeated every two days. Six days after the initial treatment, cells were fixed with formaldehyde, and stained with crystal violet (0.05%, weight/volume), a chromatin-binding cytochemical stain. The plates were washed extensively, and imaged with a flatbed scanner. For quantification of the staining, 1 ml 10% acetic acid was added to each well to extract the dye. The absorbance was measured at 590 nm with 750 nm as a reference.

Colony Formation Assay

The assays were typically performed in 12-well plate unless otherwise mentioned. Cells were suspended in medium containing 0.3% agar and plated onto a layer of 0.6% agar (for each well, 4,000 cells in 800 µl medium, 1 ml bottom agar). The wells were added with medium (without or with 100 ng/ml doxycycline) on the next day. Three weeks after seeding, the colonies were fixed with formaldehyde and imaged. The number of colonies in each well was quantified using ImageJ (National Institutes of Health).

Tumor Xenograft Studies

All xenograft studies were conducted in accordance with the animal use guidelines from the National Institutes of Health and with protocols approved by the Dana-Farber Cancer Institute Animal Care and Use Committee. The recipient mice used were NCR-nude (CrTac:NCr-Foxn1nu, Taconic). Cells were resuspended in 40% of Matrigel-Basement Membrane Matrix, LDEV-free (BD Biosciences) and sat on ice until injection. For transplanting human cell lines, mice were γ-irradiated with a single dose of 400 rads on the same day of injection. Mice were anesthesized by inhalation of isoflurane, and were injected with 150 μl cells ($5 \times 10^6$) per site. Tumors were measured in two dimensions by a caliper. Tumor volume was calculated using the formula: $V=0.5 \times length \times width \times width$. All xenograft data are presented as mean±SEM. Comparison between groups of treatment were conducted using two-tailed Student's t-test. Calculations were performed using either Openoffice or GraphPad Prism version 5.0b For the tumorigenesis study, $5 \times 10^6$ HMEC cells were injected into the mammary fat pad, and $5 \times 10^6$ Rat1 cells subcutaneously. Tumor growth was monitored twice a week. Rat1 xenografts were harvested three weeks after injection. To study the impact of MELK knockdown on tumor growth, mice were randomly sorted into groups on the second day of injection, and were left untreated or treated with doxycycline (2 mg/ml in 5% dextrose in drinking water, refreshed twice a week) for the duration of the study. Tumors were measured twice a week. To study the roles of MELK in tumor maintenance, mice with established tumors derived from orthotopic injections of MDA-MB-231, or MDA-MB-468, or MCF-7, or T47D cells were randomly sorted into two groups, with one group receiving doxycycline in drinking water. Tumors were calipered twice per week to monitor the effect of MELK knockdown on tumor growth.

Time-Lapse Imaging

Time-lapse imaging was performed on a Nikon Ti motorized inverted microscope, which was equipped with a perfect focus system and a humidified incubation chamber (37° C., 5% $CO_2$) (Nikon Imaging Center, Harvard Medical School). Cells stably expressing H2B GFP were pre-seeded in 24-well glass-bottom plate, and either left untreated or treated with doxycycline (100 ng/ml final). Images were captured every 5 minutes with a 20× objective lens, and a Hamamatsu ORCA-AG cooled CCD camera. Images were analyzed using ImageJ (National Institutes of Health).

Immunofluorescence Analysis

Cells were seeded on No. 1.5 coverslips (12 mm round) that were pre-placed into 24 well plates. Upon harvest, cells were fixed with 4% formaldehyde for 10 min. After washing, cells were permeablized with 0.1% Trition X-100 for 10 min. Cells were then washed and blocked with 1% bovine serum for 30 min before incubated with primary antibody (anti-β-tubulin, #2128, Cell Signaling Technology) prepared in PBS containing 1% bovine serum albumin. After overnight incubated at 4° C., the samples were washed and incubated with Alexa 488-conjugated secondary antibody (Invitrogen) for 1 h at room temperature. After extensive washing, the samples were dried and mounted with ProLong Antifade reagent (Invitrogen). The images were acquired with a Nikon 80i upright microscope at the Nikon Imaging Center (Harvard Medical School), which is equipped with a Hamamatsu C8484-03 monochrome camera. ImageJ was used for analysis of the images, which includes merging channels with different colors and cropping.

Immunoblotting

Cells were lysed with RIPA buffer (25 mM Tris, pH 7.4, 150 mM NaCl, 1% Nonidet P-40, 0.5% sodium deoxycholate, and 0.1% sodium dodecyl sulfate) supplemented with protease inhibitors cocktail (Roche) and phosphatase inhibitors cocktail (Thermo Scientific). Cleared lysates were analyzed for protein concentration using BCA kit (Thermo Scientific). Equal amount of protein (10-20 μg) was resolved on 8% or 10% SDS-PAGE, and was subsequently transferred onto a nitrocellulose or polyvinylidene difluoride membrane (Amersham). The membrane was blocked with 5% non-fat milk and was then incubated with primary antibodies overnight at 4° C. After washing, the membrane was incubated with fluorophore-conjugated secondary antibodies for 1 h at room temperature. The membrane was then washed and scanned with an Odyssey Infrared scanner (Li-Cor Biosciences). Primary antibodies used in this study include anti MELK (Epitomics, #2916), anti-α-tubulin (Abcam), anti-cyclin B1 (Millipore), anti-Vinculin (Sigma), anti-FoxM1 (Santa Cruz), anti-β-tubulin, anti-phopho-Akt (S473), anti-phospho Akt (T308), anti-total Akt, anti-Flag, anti-cleaved PARP (Asp214), anti-cleaved Caspase 3, anti-AURKA, anti-AURKB, anti-p27 (all from Cell Signaling Technology). Secondary antibodies used were IRDye700-conjugated anti-rabbit IgG and IRDye800-conjugated anti-mouse IgG (Rockland).

Cell Cycle Analysis

Cells were harvested by trypsinization, and repeatedly pipetted into single-cell suspension. After centrifugation, cells were fixed by adding 70% ethanol (−20° C.) dropwise while vortexing. Cells were then stained with propidium iodide (50 μg/ml, Sigma) solution containing 50 μg/ml DNase-free RNase A (Sigma) and 0.5% bovine serum albumin (BSA). After 30 min of incubation, the samples were washed and resuspended in 0.5% BSA. The analysis was performed on a LSRFortessa (BD Biosciences) at the DFCI Flow Cytometry Core Facility. Single cells were gated via plotting FL3-A to FL3-H to exclude cell debris and doublets. At least ten thousand single cells were collected for each sample.

Chromatin Immunoprecipitation

Chromatin immunoprecipitation was performed as previously described (Lee et al., 2006). Upon harvest, medium in cell culture dishes was added with 16% formaldehyde (Electron Microscopy Sciences) to reach a final concentration of 1%, and quenched with glycine (125 mM final, 5 min incubation) after incubation at room temperature for 10 min. Cells were harvested by scrapping into cold PBS, and centrifuged. Cell pellets were lysed with LB1 (50 mM HEPES, pH 7.5, 140 mM NaCl, 1 mM EDTA, 10% glycerol, 0.5% NP-40, 0.25% Triton-X-100), then after centrifugation with LB2 (10 mM Tris-HCl pH 8.0, 200 mM NaCl, 1 mM EDTA, 0.5 mM EGTA), and again after centrifugation resuspended in LB3 (10 mM Tris-HCl pH 8.0, 100 mM NaCl, 1 mM EDTA, 0.5 mM EGTA, 0.1% Na Deoxycholate, 0.5% N-lauroylsacosine). Samples were sonicated using a Q800R DNA Shearing Sonicator (Qsonica) at 50% amplitude for 10 min with a pulse of 30 seconds on and 30 seconds off. Samples were then supplemented with 10% Triton-X 100 to a final concentration of 1%, and centrifuged at 20,000×g for 10 min at 4° C. The cleared lysates were used for the following immunoprecipitation, with 50 μl of lysate saved as input.

Protein G-conjugated Dynabeads (Invitrogen) were washed with block solution (0.5% bovine serum albumin in PBS) and incubated overnight with 5 μg anti-FoxM1 (SC-502, Santa Cruz Biotechnology), or 5 μg rabbit IgG in block solution, and on the next day washed three times with block solution. Cell lysates were incubated with the antibody/magnetic bead, rotating at 4° C. overnight. On the next day, the beads were collected with magnetic stand, and washed six times with RIPA buffer (50 mM HEPES pH 7.6, 500 mM LiCl, 1 mM EDTA, 1% NP-40, 0.7% Nadeoxycholate). After a single wash with Tris-EDTA buffer containing 50 mM NaCl, samples were resuspended with elution buffer (50 mM Tris-HCl pH 8.0, 10 mM EDTA, 1% SDS) for incubation at 65° C. overnight. Also, the 50 μl input was mixed with 150 μl elution buffer and incubated at 65° C. overnight for reverse crosslinking. On the next day, RNase A was added to the samples (0.2 μg/ml final), followed by incubation for 1 h at 37° C. Samples were then treated with Proteinase K (0.2 μg/ml final) and incubated at 56° C. for 1 h. DNA were purified with a QIAquick PCR purification kit (Qiagen), and eluted with 30 μl water. PCR was performed using Quick-Load Taq 2× Master Mix (NEB), using primers listed in Table S2.

qRT-PCR Analysis

Total RNA was extracted from cultured cells with RNeasy Mini kit (Qiagen), with the use of QIAshredder spin column for homogenization and an on-column DNase digestion. Two micrograms of the total RNA was reversely transcribed using a High Capacity RNA to-cDNA Kit (Applied Biosystems). cDNAs were analyzed quantitatively using Power SYBR Green PCR Master Mix (Applied Biosystems) on an ABI7300 Real-time PCR system. Primers used were listed in Table S2. Cycling conditions were 95° C. for 15 min, 40 cycles of 15 s at 94° C., 30 s at 55° C. and 30 s at 72° C. Ct values were generated using the default analysis settings. $\Delta CT$ was defined as $Ct_{gene\ of\ interest} - Ct_{\beta actin}$. $\Delta\Delta CT$ was defined as $\Delta Ct_{treated\ sample} - Ct_{control\ sample}$. Relative quantification (RQ) was calculated as $2^{-\Delta\Delta CT}$. Statistical analysis was performed by Student's test.

Analysis of Gene Expression

Gene expression data were downloaded from Oncomine (Rhodes et al., 2004). Information of the clinical datasets is listed in Table S1. Analyses and figures were made in GraphPad Prism. In dot plot graphs, each dot indicates an individual sample, with results expressed as median with interquartile range.

Survival Analysis

Independent cohorts of breast cancer patients with overall survival or metastasis-free survival data available were examined. Information of the cohorts is listed in Table S1. Data of MELK expression and associated survival were downloaded from Oncomine (Rhodes et al., 2004). For each cohort, patients were divided into top 60% "MELK high" and bottom 40% "MELK low" groups based on the expression of MELK. Kaplan-Meier curves, as well as the log-rank (Mantel-Cox) test and the hazard ratio were analyzed by GraphPad Prism.

Statistical Analysis

Two-tailed Student's t test and ANOVA (Analysis of Variance) were used for differential comparison between two groups and among three groups, respectively. Survival and correlation analysis were performed in GraphPad Prism.

The definitions and disclosures provided herein govern and supersede all others incorporated by reference. Although the invention herein has been described in connection with preferred embodiments thereof, it will be appreciated by those skilled in the art that additions, modifications, substitutions, and deletions not specifically described may be made without departing from the spirit and scope of the invention as defined in the appended claims. It is therefore intended that the foregoing detailed description be regarded as illustrative rather than limiting, and that it be understood that it is the following claims, including all equivalents, that are intended to define the spirit and scope of this invention.

What is claimed is:

1. A method for inhibiting growth or proliferation of breast cancer cells comprising administering to a subject in need thereof in an amount that is effective to inhibit growth or proliferation of the breast cancer cells a MELK inhibitor, the MELK inhibitor comprising an inhibitory RNA having a MELK target nucleotide sequence selected from the group consisting of SEQ. ID. NO: 1, SEQ. ID. NO: 2, SEQ. ID. NO: 3 and SEQ. ID. NO: 4
wherein the inhibitory RNA comprises a nucleotide sequence selected from the group consisting of SEQ. ID. NOS: 5-12;
and wherein the breast cancer cells are estrogen receptor (ER) negative.

2. The method according to claim 1, wherein the breast cancer cells are progesterone receptor (PR) negative or human epidermal growth factor receptor 2 (HER2) negative or PR and HER2 negative.

3. A method for inhibiting growth or proliferation of breast cancer cells comprising administering to a subject in need thereof in an amount that is effective to inhibit growth or proliferation of the breast cancer cells a MELK inhibitor, a FoxM1 inhibitor or a MELK inhibitor and a FoxM1 inhibitor:
wherein the MELK inhibitor comprises an inhibitory RNA having a MELK target nucleotide sequence selected from the group consisting of SEQ. ID. NO: 1, SEQ. ID. NO: 2, SEQ. ID. NO: 3 and SEQ. ID. NO: 4,
wherein the inhibitory RNA comprises a nucleotide sequence selected from the group consisting of SEQ. ID. NOS: 5-12;
and wherein the breast cancer cells are estrogen receptor (ER) negative.

4. The method according to claim 3, wherein the breast cancer cells are progesterone receptor (PR) negative or human epidermal growth factor receptor 2 (HER2) negative or both PR negative and HER2 negative.

5. A method for treating a subject having breast cancer, the method comprising:
determining an estrogen receptor expression status in breast cancer cells of the subject;
administering a MELK inhibitor, a FoxM1 inhibitor or a MELK inhibitor and a FoxM1 inhibitor to the subject having breast cancer cells that are estrogen receptor negative;
wherein the MELK inhibitor comprises an inhibitory RNA having a MELK target nucleotide sequence selected from the group consisting of SEQ. ID. NO: 1, SEQ. ID. NO: 2, SEQ. ID. NO: 3 and SEQ. ID. NO: 4,
and wherein the inhibitory RNA comprises a nucleotide sequence selected from the group consisting of SEQ. ID. NOS: 5-12.

6. The method according to claim 5, comprising determining an progesterone receptor expression status in the breast cancer cells of the subject; and administering the MELK inhibitor, the FoxMI inhibitor or the MELK inhibitor and the FoxMI inhibitor to the subject having breast cancer cells that are estrogen receptor negative and that are progesterone receptor negative.

7. The method according to claim 5, comprising determining a human epidermal growth factor receptor 2 expression status in the breast cancer cells of the subject; and administering the MELK inhibitor, the FoxMI inhibitor or the MELK inhibitor and the FoxM1 inhibitor to the subject having breast cancer cells that are human epidermal growth factor receptor 2 negative.

* * * * *

UNITED STATES PATENT AND TRADEMARK OFFICE
CERTIFICATE OF CORRECTION

PATENT NO.        : 9,540,619 B2
APPLICATION NO.   : 14/759889
DATED             : January 10, 2017
INVENTOR(S)       : Xizhong Huang et al.

Page 1 of 1

It is certified that error appears in the above-identified patent and that said Letters Patent is hereby corrected as shown below:

In the Specification

Column 1, Line 14, after FEDERALLY SPONSORED RESEARCH OR DEVELOPMENT, please delete "This invention was made with government support under federal grant numbers CA134502, P50CA089393-08S1 and CA148164-01 awarded by the National Institutes of Health and federal grant number BC051565 awarded by the Department of Defense. The government has certain rights in the invention."

And please insert:
-- This invention was made with government support under grant numbers CA134502, CA148164, and CA089393 awarded by the National Institutes of Health and grant number W81XWH-06-1-0341 awarded by The Department of The Army. The government has certain rights in the invention. --

Signed and Sealed this
Third Day of April, 2018

Andrei Iancu
*Director of the United States Patent and Trademark Office*

SEQUENCE LISTING

```
<160> NUMBER OF SEQ ID NOS: 43

<210> SEQ ID NO 1
<211> LENGTH: 21
<212> TYPE: DNA
<213> ORGANISM: Artificial Sequence
<220> FEATURE:
<223> OTHER INFORMATION: MELK Target Sequence

<400> SEQUENCE: 1
gagagctgtt tgactatata a                                              21

<210> SEQ ID NO 2
<211> LENGTH: 21
<212> TYPE: DNA
<213> ORGANISM: Artificial Sequence
<220> FEATURE:
<223> OTHER INFORMATION: MELK Target Sequence

<400> SEQUENCE: 2
gactaaagct tcactataat g                                              21

<210> SEQ ID NO 3
<211> LENGTH: 21
<212> TYPE: DNA
<213> ORGANISM: Artificial Sequence
<220> FEATURE:
<223> OTHER INFORMATION: MELK Target Sequence
```

<400> SEQUENCE: 3
ggtgtgatac agcctacata a                                         21

<210> SEQ ID NO 4
<211> LENGTH: 21
<212> TYPE: DNA
<213> ORGANISM: Artificial Sequence
<220> FEATURE:
<223> OTHER INFORMATION: MELK Target Sequence

<400> SEQUENCE: 4
gcctgaaaga aactccaatt a                                         21

<210> SEQ ID NO 5
<211> LENGTH: 59
<212> TYPE: DNA
<213> ORGANISM: Artificial Sequence
<220> FEATURE:
<223> OTHER INFORMATION: Synthetic forward primer

<400> SEQUENCE: 5
ccgggagagc tgtttgacta taaactcga gttatatagt caaacagctc tcttttttg    59

<210> SEQ ID NO 6
<211> LENGTH: 58
<212> TYPE: DNA
<213> ORGANISM: Artificial Sequence
<220> FEATURE:
<223> OTHER INFORMATION: Synthetic reverse primer

<400> SEQUENCE: 6
aattaaaaag agagctgttt gactatataa ctcgagttat atagtcaaac agctctct    58

<210> SEQ ID NO 7
<211> LENGTH: 59
<212> TYPE: DNA
<213> ORGANISM: Artificial Sequence
<220> FEATURE:
<223> OTHER INFORMATION: Synthetic forward primer

<400> SEQUENCE: 7
ccgggactaa agcttcacta taatgctcga gcattatagt gaagctttag tcttttttg    59

<210> SEQ ID NO 8
<211> LENGTH: 58
<212> TYPE: DNA
<213> ORGANISM: Artificial Sequence
<220> FEATURE:
<223> OTHER INFORMATION: Synthetic reverse primer

<400> SEQUENCE: 8
aattaaaaag actaaagctt cactataatg ctcgagcatt atagtgaagc tttagtct    58

<210> SEQ ID NO 9
<211> LENGTH: 58
<212> TYPE: DNA
<213> ORGANISM: Artificial Sequence
<220> FEATURE:
<223> OTHER INFORMATION: Synthetic forward primer

<400> SEQUENCE: 9
ccggggtgtg atacagccta cataactcga gttatgtagg ctgtatcaca ccttttttg    58

<210> SEQ ID NO 10

```
<211> LENGTH: 58
<212> TYPE: DNA
<213> ORGANISM: Artificial Sequence
<220> FEATURE:
<223> OTHER INFORMATION: Synthetic reverse primer

<400> SEQUENCE: 10
aattcaaaaa ggtgtgatac agcctacata actcgagtta tgtaggctgt atcacacc          58

<210> SEQ ID NO 11
<211> LENGTH: 58
<212> TYPE: DNA
<213> ORGANISM: Artificial Sequence
<220> FEATURE:
<223> OTHER INFORMATION: Synthetic forward primer

<400> SEQUENCE: 11
ccgggcctga agaaactcc aattactcga gtaattggag tttctttcag gcttttttg         58

<210> SEQ ID NO 12
<211> LENGTH: 58
<212> TYPE: DNA
<213> ORGANISM: Artificial Sequence
<220> FEATURE:
<223> OTHER INFORMATION: Synthetic reverse primer

<400> SEQUENCE: 12
aattcaaaaa gcctgaaaga aactccaatt actcgagtaa ttggagtttc tttcaggc          58

<210> SEQ ID NO 13
<211> LENGTH: 30
<212> TYPE: DNA
<213> ORGANISM: Artificial Sequence
<220> FEATURE:
<223> OTHER INFORMATION: Synthetic forward primer

<400> SEQUENCE: 13
gatcaccggt atggtgagca agggcgagga                                         30

<210> SEQ ID NO 14
<211> LENGTH: 32
<212> TYPE: DNA
<213> ORGANISM: Artificial Sequence
<220> FEATURE:
<223> OTHER INFORMATION: Synthetic reverse primer

<400> SEQUENCE: 14
gatcttaatt aattacttgt acagctcgtc ca                                      32

<210> SEQ ID NO 15
<211> LENGTH: 63
<212> TYPE: DNA
<213> ORGANISM: Artificial Sequence
<220> FEATURE:
<223> OTHER INFORMATION: Synthetic forward primer

<400> SEQUENCE: 15
gatcaccggt gccaccatgg actacaaaga cgatgacgac aagaaagatt atgatgaact        60
tct                                                                      63

<210> SEQ ID NO 16
<211> LENGTH: 36
<212> TYPE: DNA
<213> ORGANISM: Artificial Sequence
<220> FEATURE:
<223> OTHER INFORMATION: Synthetic reverse primer
```

```
<400> SEQUENCE: 16
gatcttaatt aattatacct tgcagctaga taggat                                 36

<210> SEQ ID NO 17
<211> LENGTH: 36
<212> TYPE: DNA
<213> ORGANISM: Artificial Sequence
<220> FEATURE:
<223> OTHER INFORMATION: Synthetic forward primer

<400> SEQUENCE: 17
gatcggatcc gccaccatgc ctgagccagc caagtc                                 36

<210> SEQ ID NO 18
<211> LENGTH: 30
<212> TYPE: DNA
<213> ORGANISM: Artificial Sequence
<220> FEATURE:
<223> OTHER INFORMATION: Synthetic reverse primer

<400> SEQUENCE: 18
gatcctcgag cttggagctg gtgtacttgg                                        30

<210> SEQ ID NO 19
<211> LENGTH: 45
<212> TYPE: DNA
<213> ORGANISM: Artificial Sequence
<220> FEATURE:
<223> OTHER INFORMATION: Synthetic forward primer

<400> SEQUENCE: 19
tatcataaat taaagctgat tgcctttggt ctctgtgcaa aaccc                       45

<210> SEQ ID NO 20
<211> LENGTH: 45
<212> TYPE: DNA
<213> ORGANISM: Artificial Sequence
<220> FEATURE:
<223> OTHER INFORMATION: Synthetic reverse primer

<400> SEQUENCE: 20
gggttttgca cagagaccaa aggcaatcag ctttaattta tgata                       45

<210> SEQ ID NO 21
<211> LENGTH: 35
<212> TYPE: DNA
<213> ORGANISM: Artificial Sequence
<220> FEATURE:
<223> OTHER INFORMATION: Synthetic forward primer

<400> SEQUENCE: 21
aggattacca tctacaggca tgctgtggga gtctg                                  35

<210> SEQ ID NO 22
<211> LENGTH: 35
<212> TYPE: DNA
<213> ORGANISM: Artificial Sequence
<220> FEATURE:
<223> OTHER INFORMATION: Synthetic reverse primer

<400> SEQUENCE: 22
cagactccca cagcatgcct gtagatggta atcct                                  35

<210> SEQ ID NO 23
```

-continued

```
<211> LENGTH: 60
<212> TYPE: DNA
<213> ORGANISM: Artificial Sequence
<220> FEATURE:
<223> OTHER INFORMATION: Synthetic forward primer

<400> SEQUENCE: 23
caaaagctag aaaccagtgc ctgaaggaga cacctattaa ataccagta aattcaacag     60

<210> SEQ ID NO 24
<211> LENGTH: 60
<212> TYPE: DNA
<213> ORGANISM: Artificial Sequence
<220> FEATURE:
<223> OTHER INFORMATION: Synthetic reverse primer

<400> SEQUENCE: 24
ctgttgaatt tactggtatt ttaataggtg tctccttcag gcactggttt ctagcttttg     60

<210> SEQ ID NO 25
<211> LENGTH: 58
<212> TYPE: DNA
<213> ORGANISM: Artificial Sequence
<220> FEATURE:
<223> OTHER INFORMATION: Synthetic forward primer

<400> SEQUENCE: 25
ccgggtggac tcttgaaagt actatctcga gatagtactt tcaagagtcc acttttg       58

<210> SEQ ID NO 26
<211> LENGTH: 57
<212> TYPE: DNA
<213> ORGANISM: Artificial Sequence
<220> FEATURE:
<223> OTHER INFORMATION: Synthetic reverse primer

<400> SEQUENCE: 26
aattaaaaag tggactcttg aaagtactat ctcgagatag tactttcaag agtccac       57

<210> SEQ ID NO 27
<211> LENGTH: 58
<212> TYPE: DNA
<213> ORGANISM: Artificial Sequence
<220> FEATURE:
<223> OTHER INFORMATION: Synthetic forward primer

<400> SEQUENCE: 27
ccggggacca ctttccctac tttaactcga gttaaagtag ggaaagtggt cctttttg      58

<210> SEQ ID NO 28
<211> LENGTH: 58
<212> TYPE: DNA
<213> ORGANISM: Artificial Sequence
<220> FEATURE:
<223> OTHER INFORMATION: Synthetic reverse primer

<400> SEQUENCE: 28
aattcaaaaa ggaccacttt ccctacttta actcgagtta agtagggaa agtggtcc       58

<210> SEQ ID NO 29
<211> LENGTH: 19
<212> TYPE: RNA
<213> ORGANISM: Artificial Sequence
<220> FEATURE:
<223> OTHER INFORMATION: Synthetic sequence

<400> SEQUENCE: 29
```

```
ggaccacuuu cccuacuuu                                                   19

<210> SEQ ID NO 30
<211> LENGTH: 23
<212> TYPE: DNA
<213> ORGANISM: Artificial Sequence
<220> FEATURE:
<223> OTHER INFORMATION: Synthetic forward primer

<400> SEQUENCE: 30
aggctgaggc gggaggatcg ctt                                              23

<210> SEQ ID NO 31
<211> LENGTH: 24
<212> TYPE: DNA
<213> ORGANISM: Artificial Sequence
<220> FEATURE:
<223> OTHER INFORMATION: Synthetic reverse primer

<400> SEQUENCE: 31
gtgttgccac gaggaataag aacc                                             24

<210> SEQ ID NO 32
<211> LENGTH: 22
<212> TYPE: DNA
<213> ORGANISM: Artificial Sequence
<220> FEATURE:
<223> OTHER INFORMATION: Synthetic forward primer

<400> SEQUENCE: 32
aagagcccat cagttccgct tg                                               22

<210> SEQ ID NO 33
<211> LENGTH: 22
<212> TYPE: DNA
<213> ORGANISM: Artificial Sequence
<220> FEATURE:
<223> OTHER INFORMATION: Synthetic reverse primer

<400> SEQUENCE: 33
aagagcccat cagttccgct tg                                               22

<210> SEQ ID NO 34
<211> LENGTH: 20
<212> TYPE: DNA
<213> ORGANISM: Artificial Sequence
<220> FEATURE:
<223> OTHER INFORMATION: Synthetic forward primer

<400> SEQUENCE: 34
aaacccaagg gtaacaagga                                                  20

<210> SEQ ID NO 35
<211> LENGTH: 20
<212> TYPE: DNA
<213> ORGANISM: Artificial Sequence
<220> FEATURE:
<223> OTHER INFORMATION: Synthetic reverse primer

<400> SEQUENCE: 35
acagtatgcc catgctccaa                                                  20

<210> SEQ ID NO 36
<211> LENGTH: 22
<212> TYPE: DNA
```

```
<213> ORGANISM: Artificial Sequence
<220> FEATURE:
<223> OTHER INFORMATION: Synthetic forward primer

<400> SEQUENCE: 36
cttcctccca tcaacacagt cg                                        22

<210> SEQ ID NO 37
<211> LENGTH: 22
<212> TYPE: DNA
<213> ORGANISM: Artificial Sequence
<220> FEATURE:
<223> OTHER INFORMATION: Synthetic reverse primer

<400> SEQUENCE: 37
tgcttctgct gcctcttgta gg                                        22

<210> SEQ ID NO 38
<211> LENGTH: 21
<212> TYPE: DNA
<213> ORGANISM: Artificial Sequence
<220> FEATURE:
<223> OTHER INFORMATION: Synthetic forward primer

<400> SEQUENCE: 38
tcaaggacca ccgcatctct a                                         21

<210> SEQ ID NO 39
<211> LENGTH: 22
<212> TYPE: DNA
<213> ORGANISM: Artificial Sequence
<220> FEATURE:
<223> OTHER INFORMATION: Synthetic reverse primer

<400> SEQUENCE: 39
tgaagcagaa gaaacactgg gc                                        22

<210> SEQ ID NO 40
<211> LENGTH: 24
<212> TYPE: DNA
<213> ORGANISM: Artificial Sequence
<220> FEATURE:
<223> OTHER INFORMATION: Synthetic MELK target sequence

<400> SEQUENCE: 40
tgcctgaaag aaactccaat taaa                                      24

<210> SEQ ID NO 41
<211> LENGTH: 24
<212> TYPE: DNA
<213> ORGANISM: Artificial Sequence
<220> FEATURE:
<223> OTHER INFORMATION: Synthetic MELK-R target sequence

<400> SEQUENCE: 41
tgcctgaagg agacacctat taaa                                      24

<210> SEQ ID NO 42
<211> LENGTH: 17
<212> TYPE: DNA
<213> ORGANISM: Artificial Sequence
<220> FEATURE:
<223> OTHER INFORMATION: MELK promoter sequence

<400> SEQUENCE: 42
acccacaaat aatttag                                              17
```

```
<210> SEQ ID NO 43
<211> LENGTH: 10
<212> TYPE: DNA
<213> ORGANISM: Artificial Sequence
<220> FEATURE:
<223> OTHER INFORMATION: Fox M1 consensus sequence
<220> FEATURE:
<221> NAME/KEY: misc_feature
<222> LOCATION: (2)..(2)
<223> OTHER INFORMATION: n is C or T
<220> FEATURE:
<221> NAME/KEY: misc_feature
<222> LOCATION: (6)..(6)
<223> OTHER INFORMATION: n is C or T
<220> FEATURE:
<221> NAME/KEY: misc_feature
<222> LOCATION: (9)..(10)
<223> OTHER INFORMATION: n is A, C, G or T

<400> SEQUENCE: 43 anaaanaann                                                          10
```